United States Patent [19]

Renfroe

[11] Patent Number: 4,511,573

[45] Date of Patent: Apr. 16, 1985

[54] 3-SUBSTITUTED-2-(HETEROARYL) INDOLES

[75] Inventor: Harris B. Renfroe, West Nyack, N.Y.

[73] Assignee: Ciba-Geigy Corporation, Ardsley, N.Y.

[21] Appl. No.: 495,367

[22] Filed: May 17, 1983

[51] Int. Cl.³ .................. A61K 31/44; C07D 401/04; C07D 403/04

[52] U.S. Cl. .................. 514/332; 546/273; 546/270; 548/336; 514/339; 514/397

[58] Field of Search .............. 546/273, 270; 548/336; 424/263, 273 R

[56] References Cited

U.S. PATENT DOCUMENTS

| 3,468,894 | 9/1969 | Pfenninger | 424/263 |
|---|---|---|---|
| 3,557,142 | 1/1971 | Bell | 548/468 |
| 4,217,357 | 8/1980 | Cross et al. | 548/336 |
| 4,226,878 | 10/1980 | Itzuka et al. | 424/273 R |
| 4,256,757 | 3/1981 | Hayashi et al. | 424/273 R |
| 4,273,782 | 6/1981 | Cross et al. | 548/252 |
| 4,363,912 | 2/1982 | Cross et al. | 546/273 |
| 4,410,539 | 10/1983 | Cross et al. | 424/273 |
| 4,436,746 | 3/1984 | Renfroe | 424/273 |
| 4,460,777 | 7/1984 | Renfroe | 546/273 |
| 4,478,842 | 10/1984 | Renfroe | 424/263 |

FOREIGN PATENT DOCUMENTS

| 3901 | 9/1979 | European Pat. Off. |
| 73663 | 9/1983 | European Pat. Off. |
| 42-17904 | 9/1967 | Japan . |
| 2016452 | 9/1979 | United Kingdom . |
| 2038821 | 7/1980 | United Kingdom . |
| 45244 | 1/1983 | United Kingdom . |
| 2102795 | 2/1983 | United Kingdom . |

OTHER PUBLICATIONS

Buchmann, 2-Pyrdylindoles, Pharmazie 23, 557–560 (1968) C.A. 70, 472365/(1969).
Sugasawa et al., Pharm. Bull. Japan 4, 16–19 (1956).
Buchmann et al., CA 64, 19540d (1966).
Fetizon et al., Bull. Soc. Chim., France, 1969, 4154–4159.
Takahashi et al., Chem. Abstracts, 1964, 1694d.
Fetizon et al., Bull. Soc. Chem., France, 1966, 771–772.
Kahnt et al., Acta Endocrinologica 70, 315–330 (1972).

Primary Examiner—Jane T. Fan
Attorney, Agent, or Firm—Norbert Gruenfeld

[57] ABSTRACT

Disclosed as thromboxane synthetase inhibitors are the compounds of formula

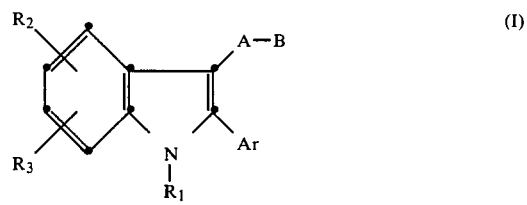

wherein $R_1$ represents hydrogen or lower alkyl;

Ar represents 3-pyridyl or 1-imidazolyl, each unsubstituted or substituted by lower alkyl, carboxy, lower alkoxycarbonyl or carbamoyl;

$R_2$ and $R_3$ independently represent hydrogen, lower alkyl, halogen, trifluoromethyl, hydroxy, lower alkoxy, carboxy lower alkyl, lower alkoxycarbonyl lower alkyl, carboxy, lower alkoxycarbonyl, or lower alkyl-(thio, sulfinyl or sulfonyl), or $R_2$ and $R_3$ together on adjacent carbon atoms represent lower alkylenedioxy;

A represents straight chain or branched alkylene of 3 to 12 carbon atoms in which the number of the carbon atoms separating the indole nucleus from group B is 3 to 12, straight chain or branched alkenylene of 2 to 12 carbon atoms, straight chain or branched alkynylene of 2 to 12 carbon atoms, lower alkylenephenylene-lower (alkylene or alkenylene), lower alkylenephenylene, lower alkylene-(thio or oxy)-lower alkylene, lower alkylene-(thio or oxy)-phenylene, or lower alkylenephenylene-(thio or oxy)-lower alkylene;

B represents carboxy, esterified carboxy, carbamoyl, mono- or di-lower alkylcarbamoyl, hydroxymethyl, cyano, hydroxycarbamoyl, 5-tetrazolyl or formyl; the imidazolyl and pyridyl N-oxide thereof; or a pharmaceutically acceptable salt thereof; as well as their synthesis, pharmaceutical compositions thereof, and methods of treatment utilizing such compounds.

20 Claims, No Drawings

3-SUBSTITUTED-2-(HETEROARYL) INDOLES

BACKGROUND OF THE INVENTION

U.S. Pat. No. 3,468,894 discloses the 1-unsubstituted 3-methyl-2-(3- or 4-pyridyl)indoles as diuretic agent. 2-(2-Pyridyl)indole-3-(acetic, propionic) acids are reported, e.g., in Pharm. Bull. 4, 16 (1956) and Chemical Abstracts 64, 19540d (1966) respectively. Various optically substituted 2-(3-pyridyl)-indole-3-acetic acids are described as chemical intermediates in Bull. Soc. Chim. France 1966, 771–2 and Bull. Soc. Chim. France 1969, 4154–9. The preparation of 1-cyanoethyl-2-(2-pyridyl)-indole is reported in Pharmazie 23, (10), 557–60 (1968).

Reported as thromboxane synthetase inhibitors are, e.g., 3-(imidazol-1-yl-alkyl)indones of U.S. Pat. Nos. 4,217,357 and 4,273,782, and 1-substituted imidazoles, e.g., U.S. Pat. Nos. 4,226,878 and 4,256,757 and British Patent Application Nos. 2,016,452A and 2,038,821A.

The present invention is concerned with the 2-(pyridyl and imidazolyl)-indoles of formula I which are useful as surprisingly potent and highly specific thromboxane synthetase inhibitors.

The foregoing attributes render the 2-(heteroaryl)-indoles of this invention particularly useful when administered, alone or in combination, to mammals, e.g. for the treatment or prevention of diseases responsive to the inhibition of thromboxane synthetase, comprising cardiovascular disorders such as peripheral vascular diseases and Raynaud's syndrome, thrombosis, atherosclerosis, coronary spasm, arrhythmias, cerebral ischaemic attacks, migraine and other vascular headaches, myocardial infarction, angina pectoris, hypertension; respiratory disorders, such as asthma and apnea; and inflammatory disorders.

SUMMARY OF THE INVENTION

This invention relates to 2-(pyridyl and imidazolyl)indoles of formula I which are useful as selective thromboxane synthetase inhibitors, processes for preparing same, pharmaceutical compositions comprising said compounds, and methods of treating syndromes, conditions and diseases in mammals responsive to the inhibition of thromboxane synthetase by administration of said compounds and compositions.

DETAILED DESCRIPTION OF THE INVENTION

Particularly the invention relates to the 2-heteroacrylindoles of formula I

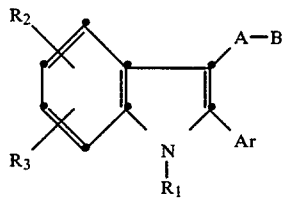

wherein $R_1$ represents hydrogen or lower akyl;

Ar represents 3-pyridyl or 1-imidazolyl, each unsubstituted or substituted by lower alkyl, carboxy, lower alkoxycarbonyl or carbamoyl;

$R_2$ and $R_3$ independently represent hydrogen, lower alkyl, halogen, trifluoromethyl, hydroxy, lower alkoxy, carboxy lower alkyl, lower alkyoxycarbonyl lower alkyl, carboxy, lower alkyoxycarbonyl, or lower alkyl-(thio, sulfinyl or sulfonyl), or $R_2$ and $R_3$ together on adjacent carbon atoms represent lower alkylenedioxy;

A represents straight chain or branched alkylene of 3 to 12 carbon atoms in which the number of the carbon atoms separating the indole nucleus from group B is 3 to 12, straight chain or branched alkenylene of 2 to 12 carbon atoms, straight chain or branched alkynylene of 2 to 12 carbon atoms, lower alkylenephenylene-lower (alkylene or alkenylene), lower alkylenephenylene, lower alkylene-(thio or oxy)-lower alkylene, lower alkylene-(thio or oxy)-phenylene, or lower alkylenephenylene-(thio) or oxy)-lower alkylene;

B represents carboxy, esterified carboxy, carbamoyl, mono- or di-lower alkylcarbamoyl, hydroxymethyl, cyano, hydroxycarbamoyl, 5-tetrazolyl or formyl; the imidazolyl and pyridyl N-oxides thereof; and pharmaceutically acceptable salts thereof.

Preferred embodiments of this invention relate to compounds of formula I wherein $R_1$ represents hydrogen or lower alkyl;

Ar represents 3-pyridyl, 1-imidazolyl, 3-pyridyl substituted by lower alkyl, or 1-imidazolyl substituted by lower alkyl;

$R_2$ and $R_3$ independently represent hydrogen, lower alkyl, halogen, trifluoromethyl, hydroxy, lower alkoxy or lower alkyl-thio; or $R_2$ and $R_3$ together on adjacent carbon atoms represent lower alkylenedioxy;

A represents straight chain alkylene of 4 to 12 carbon atoms, lower(alkylenephenylene, alkylene-thio-phenylene or alkylene-oxy-phenylene) of 7 to 10 carbon atoms each;

B represents carboxy, lower alkoxycarbonyl, carbamoyl, cyano, hydroxcarbamoyl, 5-tetrazolyl, or hydroxymethyl; and pharmaceutically acceptable salts thereof.

Further preferred are said compounds of formula I wherein $R_2$ is attached at the 5-position of the indole nucleus and $R_3$ is hydrogen.

Partically preferred are said compounds of formula I wherein B represents carboxy, lower alkoxycarbonyl, carbamoyl, 5-tetrazolyl or hydroxycarbamoyl.

Greatly preferred are the compounds of formula I wherein A represents straight chain alkylene of 4 to 10 carbon atoms, lower alkylenephenylene 7 to 10 carbon atoms, lower alkylene-thio-phenylene of 7 to 10 carbon atoms or lower alkylene-oxy-phenylene of 7 to 10 carbon atoms; B represents carboxy or lower alkoxy-carbonyl; Ar represents 3-pyridyl or 1-imidazolyl; $R_2$ and $R_3$ independently represent hydrogen, lower alkyl, halogen, trifluoromethyl, hydroxy, lower alkylthio or lower alkoxy; and pharmaceutically acceptable salts thereof.

Most preferred are the said compounds of formula I wherein A represents straight chain alkylene of 4 to 8 carbon atoms.

A particularly preferred embodiment of the invention is represented by compounds of formula II

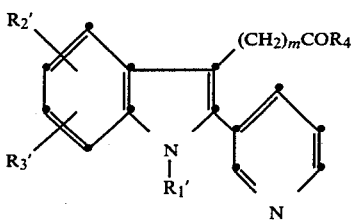

wherein

R$_1$' represents hydrogen or lower alkyl;

R$_2$' and R$_3$' represent independently hydrogen, lower alkyl, halogen, trifluoromethyl, hydroxy, lower alkylthio or lower alkoxy; or R$_2$' and R$_3$' together on adjacent carbon atoms represent methylenedioxy;

m represents an integer from 4 to 12;

R$_4$ represents hydroxy, lower alkoxy or amino; and pharmaceutically acceptable salts thereof.

Preferred are the compounds of formula II wherein R$_3$' represents hydrogen.

Further preferred are compounds of formula II wherein

R$_1$' represents methyl, ethyl, propyl;

R$_2$' represents hydrogen, methyl, chloro, fluoro, trifluoromethyl, hydroxy, methylthio or methoxy; R$_3$' represents hydrogen;

m represents an integer from 4 to 8;

R$_4$ represents hydroxy, ethoxy, methoxy or amino; and pharmaceutically acceptable salts thereof.

Especially preferred are the compounds of formula II wherein R$_1$' represents hydrogen or lower alkyl; R$_2$' represents hydrogen or halogen; R$_3$' represents hydrogen; m is 4 to 8; R$_4$ represents hydroxy, lower alkoxy or amino; and pharmaceutically acceptable salts thereof.

Most preferred are the compounds of formula II wherein R$_1$' represents hydrogen or methyl; R$_2$' represents hydrogen or chloro; R$_3$' represents hydrogen; m is 5; R$_4$ represents hydroxy; and pharmaceutically acceptable salts thereof.

Another preferred embodiment of the invention is represented by the compounds of formula III

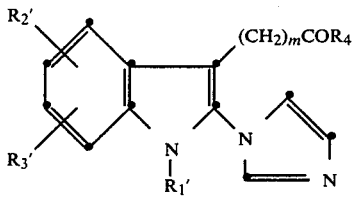

wherein

R$_1$' represents hydrogen or lower alkly;

R$_2$' and R$_3$' represent independently hydrogen, lower alkyl, halogen, trifluoromethyl, hydroxy, lower alkylthio or lower alkoxy; or R$_2$' and R$_3$' together on adjacent carbon atoms represent methylenedioxy;

m represents an integer from 3 to 12;

R$_4$ represents hydroxy, lower alkoxy or amino; and pharmaceutically acceptable salts thereof.

Preferred are the compounds of formula III wherein R$_3$' represents hydrogen.

Further preferred are compounds of formula III wherein

R$_1$' represents methyl, ethyl, propyl;

R$_2$' represents hydrogen, methyl, chloro, fluoro, trifluoromethyl, hydroxy, methylthio or methoxy; R$_3$' represents hydrogen;

m represents an integer from 3 to 8;

R$_4$ represents hydroxy, ethoxy, methoxy or amino; and pharmaceutically acceptable salts thereof.

Especially preferred are the compounds of formula III wherein R$_1$' represents hydrogen or lower akyl; R$_2$' represents hydrogen or halogen; R$_3$' represents hydrogen; m is 4 to 8; R$_4$ represents hydroxy, lower alkoxy or amino; and pharmaceutically acceptable salts thereof.

Most preferred are the compounds of formula III wherein R$_1$' represents hydrogen or methyl; R$_2$' represents hydrogen or chloro; R$_3$' represents hydrogen; m is 5; R$_4$ represents hydroxy; and pharmaceutically acceptable salts thereof.

The general definitions used herein have the following meanings within the scope of the present invention.

The term "straight chain or branched alkylene of 3 to 12 carbon atoms" represents preferably propylene, butylene, pentylene, hexylene, or heptylene, said radicals being unsubstituted or substituted by one or more lower alkyl groups with the proviso that the total number of carbon atoms equals no more than 12.

The term "straight chain or branched alkenylene of 2 to 12 carbon atoms" represents preferably propenylene, 1- or 2-butenylene, 1- or 2-pentenylene, 1-, 2- or 3-hexenylene, 1-, 2-, 3- or 4-heptenylene, said groups being unsubstituted or substituted by one or more lower alkyl groups with the provisio that the total number of carbon atoms equals no more than 12.

The term "straight chain or branched alkynylene" represents C$_2$–C$_{12}$ alkynylene preferably propynylene, 1- or 2-butynylene, 1- or 2-pentynylene, 1-, 2- or 3-hexynylene, 1-, 2-, 3- or 4-heptynylene, said radicals being unsubstituted or substituted by one or more lower alkyl groups with the proviso that the total number of carbon atoms equals no more than 12.

The term phenylene represents 1,2-, 1,3- and preferably 1,4-phenylene.

The term "lower" when referred to above and hereinafter in connection with organic groups, radicals or compounds respectively defines such with up to and including 7, preferably up to and including 4 and advantageously one, two or three carbon atoms.

A lower alkylenephenylene group, a lower alkylenephenylene-lower (alkylene or alkenylene) group, a lower alkylene-(thio or oxy)-phenylene group, preferably contains 1 to 4 carbon atoms and advantageously one or two carbon atoms in each alkylene or 2 to 4 carbon atoms in each alkenylene portion. The lower alkylene and alkenylene portions may be straight chain or branched.

A lower alkylene-(thio or oxy)-lower alkylene group is straight chain or branched and may contain a total of 2 to 12 carbon atoms, preferably 2 to 8 carbon atoms.

A lower alkyl group preferably contains 1–4 carbon atoms and represents for example ethyl, propyl, butyl or advantageously methyl.

A lower alkylene group preferably contains 1–4 carbon atoms and represents for example methylene, ethylene, 1,2- or 1,3-propylene, 1,2- 1,3- or 1,4-butylene.

A lower alkylenedioxy group represents preferably ethylenedioxy and methylenedioxy.

A lower alkoxy group preferably contains 1–4 carbon atoms and represents for example, ethoxy, propoxy or advantageously methoxy. A lower alkyl-(thio, sulfinyl or sulfonyl) group represents advantageously methylthio, methylsufinyl or methylsulfonyl respectively.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl. A mono(lower alkyl)-carbamoyl group preferably contains 1–4 carbon atoms in the alkyl portion and is for example N-methylcarbamoyl, N-propylcarbamoyl, or advantageously N-ethylcarbamoyl. A di(lower alkyl)-carbamoyl group preferably contains 1–4 carbon atoms in each lower alkyl portion and represents for example N,N-dimethylcarbamoyl, N-methyl-N-ethylcarbamoyl and advantageously N,N-diethylcarbamoyl.

Halogen is preferably fluorine and chlorine, but may also represent bromine or iodine.

Esterified carboxy represents preferably carboxy esterified in form of a pharmaceutically acceptable ester, advantageously an ester that may be convertible by solvolysis or under physiological conditions to the free carboxylic acid, e.g. lower alkoxy carbonyl; (amino, mono- or di-lower akylamino)substituted lower alkoxycarbonyl; carboxy substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. optionally substituted benzyloxy carbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1-]heptyloxycarbonyl-substituted methoxy such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl.

Pharmaceutically acceptable salts are preferably metal or ammonium salts or said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono- di- or tri-lower (alkyl, cycloalkyl or hydroxyalkyl)-amines, lower alkylenediamines or lower (hydroxyalkyl or aralkyl)-alkylammonium hydroxides, e.g., methylamine, diethylamine, triethylamine, dicyclohexylamine, triethanolamine, ethylenediamine, tris-(hydroxymethyl)aminomethane or benzyltrimethylammonium hydroxide. Said compounds of Formula I form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively decreasing thromboxane levels through selective inhibition of thromboxane synthetase in mammals. The compounds are thus useful for treating diseases responsive to thromboxane synthetase inhibition in mammals, primarily cardiovascular disorders such as thrombosis, atherosclerosis, coronary spasm, cerebral ischaemic attacks, migraine and other vascular headaches, myocardial infarction, angina pectoris, and hypertension.

These effects are demonstrable in in vitro tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 to 100 mg/kg/day, preferably between about 0.05 and 50 mg/kg/day, advantageously between about 0.1 and 25 mg/kg/day.

The in vitro inhibition of the thromboxane synthetase exzyme can be demonstrated, analogous to the method of Sun, Biochem. Biophys. Res. Comm. 74, 1432 (1977); the testing procedure is as follows:

$^{14}$C-Arachiodonic acid is incubated with an exzyme consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin E2 (PGE$_2$) is reduced to a mixture of Prostaglandin F$_2\alpha$ and F$_2\beta$ (PGF$_2\alpha+\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene: acetone: glacial acetic acid (100 volumes: 100 volumes: 3 volumes). The radioactive zones are located; those corresponding to Thromboxane B$_2$ (TxB$_2$) and PGF$_2\alpha+\beta$ are transferred to liquid scintillation vials and counted. The ratio of counts for TxB$_2$/PGF$_2\alpha+\beta$ is calculated for each concentration of test compound and IC$_{50}$ values are determined graphically as the concentration of test compound at which the ratio of T×B$_2$/PGE$_2\alpha+\beta$ is reduced to 50% of the control value.

The in-vitro effect on prostaglandin cyclooxygenase is measured by a modification of the method of Takeguchi et al. described in Biochemistry 10, 2372 (1971); the testing procedure is as follows:

Lyophilized sheep seminal vesicle microsomes are utilized as the prostaglandin-synthesizing enzyme preparation. The conversion of $^{14}$C-arachidonic acid to PGE$_2$ is measured. Test compounds (dissolved in buffer, or if necessary, in a small amount of ethanol) are added to the incubation mixture. The prostaglandins are extracted and separated by thin-layer chromatography; the plates are scanned, the radioactive zones corresponding to PGE$_2$ are transferred to liquid scintillation vials and counted for radioactivity. IC$_{50}$ values for inhibition are determined graphically as the concentration of test compound causing a 50% reduction in the amount of $PGE_2$ synthesized.

The in-vitro effect on prostacyclin ($PGI_2$) synthetase is measured analogous to the method of Sun et al., Prostaglandins 14, 1055 (1977);

The testing procedure is as follows:

$^{14}C$-Arachiodonic acid is incubated with an enzyme mixture consisting of solubilized and partially purified prostaglandin cyclo-oxygenase from sheep seminal vesicles and crude $PGI_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al.. The radioactive zones are located with a scanner; those corresponding to 6-keto-$PGF_1\alpha$(a stable end product of prostacyclin biotransformation) and $PGE_2$ are transferred to liquid scintillation vials and counted. The ratio of counts for 6-keto-$PGF_1\alpha/PGE_2$ is calculated for each concentration of test compound used. $IC_{50}$ values for inhibition are determined graphically as the concentration of test compound at which the ratio of 6-keto-$PGF_1\alpha/PGE_2$ is reduced to 50% of the control value.

The inhibition of the synthesis and the reduction of plasma levels of thromboxane is determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the inonophore injection. A single aliquot of each plasma sample is assayed for thromboxane $B_2$ and another aliquot for 6-keto-$PGF_1\alpha$, the stable metabolites of thromboxane $A_2$ and prostacyclin ($PGI_2$) respectively, by radioimmunoassay.

Compounds of the formula I are very potent and selective, thromboxane synthetase inhibitors. At the effective dose levels for thromboxane synthetase inhibition neither the beneficial prostacyclin synthetase enzyme system nor the prostaglandin cyclooxygenase enzyme system is signficantly inhibited. The prostacyclin levels are actually significantly increased.

Illustrative of the invention, the $IC_{50}$ for 3-(5-carboxypentyl)-1-methyl-2-(3-pyridyl)indole is $2.2 \times 10^{-9}M$ for thromboxane synthetase inhibition whereas the $IC_{50}$ for both inhibition of prostacyclin synthetase and cyclooxygenase is several orders of magnitude higher, i.e. about $1 \times 10^{-4}M$.

Further illustrative of the invention the $IC_{50}$ for thromboxane synthetase inhibition is e.g. about $1.7 \times 10^{-9}M$ for 3-(5-carboxypentyl)-2-(3-pyridyl)indole, about $2 \times 10^{-9}M$ for 3-(5-carboxypentyl)-5-chloro-2-(3-pyridyl)indole, and about $7 \times 10^{-10}M$ for 3-(5-carboxypentyl)-5-chloro-1-methyl-2-(3-pyridyl)indole.

3-(5-Carboxypentyl)-5-chloro-1-methyl-2-(3-pyridyl)indole, as a representative illustrative compound of the invention, decreases the plasma concentration of thromboxane $B_2$ by over 50% in the rat at an oral dose as low as 0.10 mg/kg; a surprising approximately 8 fold increase in the plasma level of prostacyclin is observed at this dose.

The aforementioned advantageous properties render the compounds of this invention of great value as specific therapeutic agents for mammals including man.

Indicative of the utility in thromboembolism, compounds of this invention, e.g. 3-(5-carboxypentyl)-1-methyl-2-(3-pyridyl)indole inhibits variously induced platelet aggregation and thrombocytopenia. Experimentally, prolongation of bleeding time in the rat is indicative of a beneficial antithrombotic effect. The compounds of this invention prolong bleeding time, e.g. 3-(5-carboxypentyl)-2-(3-pyridyl)indole prolongs bleeding time when administered orally to rats at a dose of about 10 mg/kg.

In addition to the pharmaceutically acceptable salts cited above, any prodrug derivatives thereof, e.g., pharmaceutically acceptable esters and amides of the carboxylic acids of this invention that may be convertible by solvolysis or under physiological conditions to the said carboxylic acids, represent a further object of this invention.

Said prodrug esters are preferably e.g., the straight chain or branched lower alkyl esters unsubstituted or suitably substituted such as the pivaloyloxymethyl, 2-diethylaminoethyl, bornyloxycarbonylmethyl, α-carboxyethyl or suitably esterified α-carboxyethyl esters and the like which are prepared by methods well known to the art.

Said prodrug amides are preferably e.g. simple primary and secondary amides and amides derived from the amino acids or derivatives thereof, such as the amides derived from alanine, phenylalanine and the like.

The compounds of formula I according to the invention can be prepared by processes comprising, e.g.

(1) condensing a compound of the formula IV

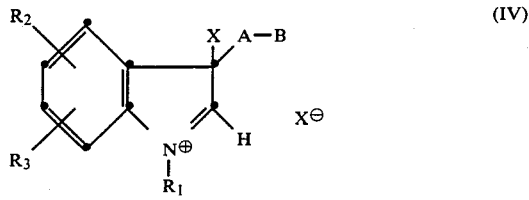

wherein $R_1$, $R_2$, $R_3$, A and B have meaning as previously described, and X represents halogen, With a compound of the formula ArH or a reactive metallic derivative thereof in which Ar has meaning as previously described; and, if required, alkylating a resulting compound of formula I wherein $R_1$ is hydrogen to a compound of formula I wherein $R_1$ is lower alkyl.

(2) condensing a compound of the formula V

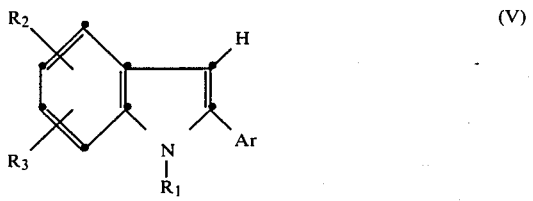

wherein $R_1$, $R_2$, $R_3$ and Ar have meaning as defined above, as a reactive metallic derivative thereof, with a reactive functional derivative of a compound of the formula VI

HO—A—B     (VI)

wherein A and B have meaning as defined above, with optional temporary protection of interfering reactive groups; and, if required, alkylating a resulting compound of formula I wherein $R_1$ is hydrogen to a compound of formula I wherein $R_1$ is lower alkyl;

(3) ring-closing a compound of formula VII

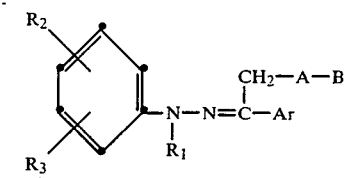     (VII)

wherein $R_1$, $R_2$, $R_3$, A and B have meaning as defined above and Ar represents 3-pyridyl or 3-pyridyl substituted as defined above;

(4) cyclizing a compound of the formula VIII

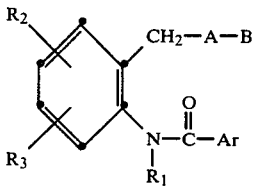     (VIII)

wherein Ar, $R_1$, $R_2$, $R_3$, A and B have meaning as defined above; and Ar preferably represents 3-pyridyl or 3-pyridyl substituted as defined above; or (5) converting into a compound of formula I a compound of the formula Ia

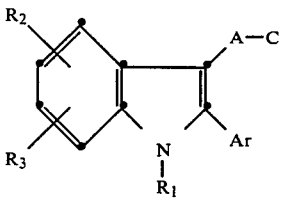     (Ia)

wherein A, Ar, $R_1$, $R_2$ and $R_3$ have meaning as defined above and C is a group differing from B and convertible into B; and/or if desired, converting a resulting compound of formula I obtained by any of the above processes into another compound of formula I, and/or if desired, converting a resulting compound of formula I obtained by any of the above processes into a salt thereof, or liberating a free compound from such salt; and/or if appropriate, isolating an optical or geometric isomer which is enriched from a mixture of isomeric forms of a resulting compound of formula I.

For the condensation according to process (1) the compounds of formula IV are first preferably prepared in situ by treatment of a compound of formula IVa

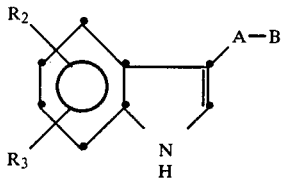     (IVa)

wherein $R_2$, $R_3$, A and B have meaning as previously described with a halogen, preferably bromine in an inert solvent such as dioxane, advantageously at room temperature.

Subsequent condensation with a compound ArH or a reactive metallic derivative thereof, e.g. by an alkali metal derivative, is carried out at a temperature range of 0° C. to 100° C., advantageously at room temperature.

Process (1) is most advantageous for the preparation of the compounds of Formula I wherein Ar represents 1-imidazolyl, or 1-imidazolyl substituted by lower alkyl, and ArH represents imidazole or imidazolyl substituted on carbon by lower alkyl.

The starting indoles of formula IVa are either known or if new are prepared by methods well-known in the art.

For the condensation according to process (2), the compounds of formula V are first converted to reactive organometallic derivatives, e.g., the alkali metal or halomagnesium (Grignard) derivatives with an appropriate metallizing agent e.g. a Grignard reagent, an alkali metal base or a quaternary ammonium base. More specifically, compounds of formula V are converted preferably in situ, to reactive oganometallic intermediates with a reactive metallizing agent, preferably about one molar equivalent of e.g. a strong alkali metal base, such as lithium diisopropylamide, sodium hydride, potassium t-butoxide, a Grignard reagent e.g. a lower alkyl magnesium halide such as methyl or ethylmagnesium bromide in an inert solvent such as dimethylformamide, diethyl ether or tetrahydrofuran at a temperature range between $-50°$ to $+75°$ preferably between $-25°$ and $+50°$. Condensation of the resulting reactive organometallic compound of formula V with a reactive esterified derivative of a compound of formula VI proceeds at a temperature range from about $-25°$ to $+50°$, preferably at a temperature range of 0° to 30°. In the case where B represents carboxy, carbamoyl, hydroxycarbamoyl, mono lower alkylcarbamoyl, an additional e.g. one molar equivalent of metallizing agent is required.

The intermediates of formula V are either known to the art (e.g. U.S. Pat. No. 3,468,894; J. Chem. Soc. 1955, 2865; Bull. Soc. Chim. France 1969, 4154) or are prepared analogously from the corresponding optionally substituted phenylhydrazines and ketones of the formula ArCOCH$_3$ in the presence of a condensing agent, e.g. ethanolic HCl or polyphosphoric acid by the well-known Fischer indole synthesis.

The starting materials of formula VI are known or if new, are prepared according to conventional methods, e.g. the methods illustrated in U.S. Pat. No. 4,256,757, British patent application No. 2,016,452A.

The ring closure according to process (3) of the intermediates of formula VII is carried out by the well-known Fischer indole synthesis [as described e.g. in "Heterocyclic Compounds, Indoles Part I" edited by W. J. Houlihan pp. 232-317] thermally or preferably in the presence of an acid condensing agent, advantageously a hydrogen halide, e.g. ethanolic hydrogen chloride, or polyphosphoric acid, optionally in an inert solvent preferably at a temperature of about 50°–100° C.

The intermediate hydrazones of formula VII are either isolated or are preferably prepared in situ by the condensation of a ketone of the formula ArCOCH$_2$—A—B, wherein Ar A and B have the meaning as previously described for the compounds of formula I, with a hydrazine of the formula IX

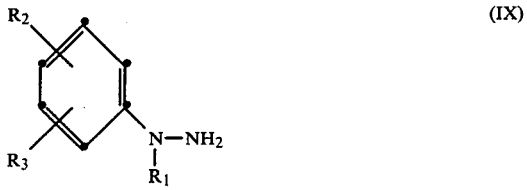

(IX)

wherein the symbols $R_1$, $R_2$ and $R_3$ have meaning as peviously defined for the compounds of formula I, advantageously in the presence of an acid catalyst.

The starting hydrazines of formula IX are known or are in turn preferably prepared by e.g. nitrosation of the correspondingly substituted anilines of formula X

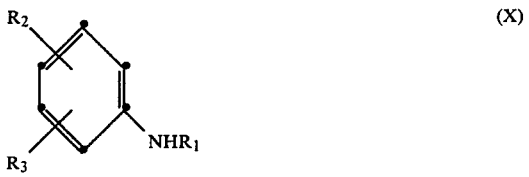

(X)

wherein the symbols $R_1$, $R_2$ and $R_3$ have meaning as previously defined, and subsequent reduction of the N-nitroso derivatives, e.g. with zinc in acetic acid or by other methods well-known to the art.

The cycliazation according to process (4) is carried out under conditions of the Madelung indole synthesis as described in "Heterocyclic Compounds, Indoles Vol. I", edited by W. J. Houlihan, pp. 385–396. The intramolecular cyclization is preferably carried out in the presence of a strong base, e.g. sodium ethoxide, sodium amide, potassium t-butoxide advantageously at elevated temperature e.g. ca. 300° neat or in an inert high boiling solvent such as tetrahydronaphthalene.

The intermediate of formula VIII are prepared by acylation of the substituted anilines of formula XI

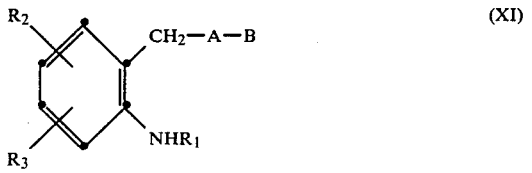

(XI)

wherein A, B, $R_1$, $R_2$ and $R_3$ have meaning as previously defined, with a compound of the formula ArCOOH wherein Ar preferably represents 3-pyridyl or 3-pyridyl substituted as defined above, or a reactive functional derivative thereof.

The conversion of a compound of formula Ia according to a process (5) wherein C differs from B into a compound of formula I, and the optional conversion of resulting product of formula I into another compound of this invention are performed by chemical methodology known to the art, and/or e.g. as described herein.

A convertible group C preferably represents trialkoxymethyl, esterified hydroxymethyl, etherified hydroxynmethyl, halomethyl, 2-oxazolinyl, dihydro-2-oxazolinyl, lower alkanoyloxymethyl, acetyl, methyl, carboxycarbonyl, trihaloacetyl, di(lower)alkoxymethyl, alkylenedioxymethyl, vinyl, alkynyl, esterified carboxy, amidated carboxy.

The intermediate of formula Ia are prepared according to processes 1 to 3 and/or as described herein, using conventional chemical methodology well known to the art.

Compounds of formula I or Ia, e.g. wherein A represents alkenylene may be prepared by (a) condensing a compound of formula V with an N,N-disubstituted formamide under conditions of the Vilsmeier-Haack reaction, e.g. with dimethylformamide in the presence of phosphorus oxychloride, and (b) condensing under conditions of a Wittig reaction the resulting 3-formyl derivative of a compound of formula V with an ylid of a compound of formula XII or XIIa

$R_5$—A′—B          (XII)

$R_5$—A′—C          (XIIa)

wherein B and C are as previously defined; A′ is e.g. alkylene as previously defined for compounds of formula I but with the chain length shortened by 1 carbon atom; and $R_5$ represents a dialkylphosphono (e.g. diethylphosphono) or a triarylphosphonium (e.g. triphenylphosphonium) radical.

Compounds of formula I or Ia, e.g. wherein A represents lower alkylene-(thio or oxy)-lower alkylene or lower alkylene(thio or oxy)-phenylene, may also be prepared by (a) treatment of a compound of formula V under conditions of the Mannich reaction, e.g. with formaldehyde and a secondary amine (e.g. dimethylamine); and (b) reacting the resulting 3-(disubstituted aminomethyl) derivative of a compound of formula V with e.g. a compound of the formula XIII or XIIIa

$R_5′$—R″—B          (XIII)

$R_5′$—A″—C          (XIIIa)

or a reactive alkali metal or ammonium derivative thereof, wherein B and C are as previously defined; $R_5′$ represents hydroxy or thiol; and A″ represents e.g. lower alkylene or phenylene; or e.g. with a lactone or thiolactone of a compound of formula XIII wherein $R_5′$ is hydroxy or thiol; A″ is lower alkylene and B is carboxy.

If any intermediates contain interfering reactive groups, e.g. carboxy, hydroxy or amino groups, such may advantageously be temporarily protected at any stage with easily removable blocking groups, e.g. in the form of esters or amides by methods well known to the art.

Certain terms used in the foregoing processes have the meaning as defined below.

Reactive functional derivatives of alcohols of formula VI are e.g. such esterified by a strong inorganic or organic acid above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)-methyl, particularly triethoxy- or trimethoxymethyl.

Etherified hydroxymethyl represents preferably tertiary lower alkyloxymethyl, lower alkoxyalkoxymethyl such as methoxymethyloxymethyl, 2-oxa- or 2-thiacycloalkoxymethyl particularly 2-tetrahydropyranyloxymethyl.

Esterified hydroxymethyl represents preferably lower alkanoyloxymethyl, advantageously acetoxymethyl.

Halomethyl represents especially chloromethyl but may also be bromomethyl or iodomethyl.

An alkali metal represents preferably lithium but may also be potassium or sodium.

The conversion of the compounds of formula Ia to compounds of formula I and the interconversions of the compounds of this invention are carried out by chemical methodology well-known to the art.

Intermediates of formula Ia wherein C is halomethyl may be reacted preferably with a metal cyanide such as potassium cyanide in a conventional manner to yield the conpounds of formula I wherein the chain is extended by 1 carbon atom and B is cyano. These in turn are converted to compounds of formula I wherein B is carboxy, alkoxycarbonyl or carbamoll using methods known to the art.

Thus, the compounds of formula I wherein B represents cyano (nitriles) are converted to compounds of formula I wherein B is carboxy by hydrolysis with inorganic acids e.g. a hydrohalic acid such as hydrochloric acid or sulfuric acid in aqueous solution, or advantageously byhydrolysis with aqueous alkali metal hydroxide e.g. potassium hydroxide at reflux temperature.

The conversion of said nitriles to compounds of formula I wherein B represents lower alkoxycarbonyl is advantageously carried out by treatment first with a lower alkanol, e.g. anhydrous ethanol, in the presence of a strong acid, e.g. hydrochloric acid preferably at reflux temperature, followed by careful hydrolysis with water.

Furthermore, the conversion of the said nitriles to compounds of formula I wherein B represents carbamoyl is preferably carried out by treatment with an alkali metal hydroxide, e.g. dilute sodium hydroxide, and hydrogen peroxide, preferably at room temperature.

Furthermore, the intermediates of formula Ia wherein C is halomethyl, such as chloromethyl, are converted to compounds of formula I, wherein B is carboxy and the chain length is extended by two carbons, by first treating with e.g. a di-(lower) alkyl malonate, such as diethyl malonate, in the presence of a base such as potassium carbonate or sodium ethoxide, in a solvent such as dimethylformamide, preferably at a temperature range from 50° to 100°. The resulting substituted di(lower)alkyl malonate is hydrolyzed, advantageously with aqueous base, such as dilute sodium hydroxide, to the corresponding malonic acid which is decarboxylated under standard conditions, e.g. by heating in xylene solution, to give a compound of formula I wherein B is carboxy. Substitution of the di-(lower)alkyl malonate with a lower alkyl cyanoacetate yields the corresponding compounds of formula I wherein B is cyano.

Compounds of the invention, wherein A represent straight chain or branched alkenylene with a terminal double bond, may also be prepared from intermediates of formula Ia wherein C is halomethyl. For instance, said intermediates are first treated with e.g. a lower alkyl ester of an α-(aryl- or alkyl) thioacetic acid such as ethyl α-(phenylthio)- acetate, in the presence of a strong base such as sodium hydride. Subsequent oxidation of the resulting α-arylthio or α-alkylthio substituted ester to the α-arylsulfinyl or 60-alkylsulfinyl ester with e.g. sodium periodate, followed by heat-induced elimination, by e.g. refluxing in xylene, yields a compound of general formula I (an αβ-unsaturated ester) wherein A represents alkylene and B represents e.g. lower alkoxycarbonyl, and the chain length has been extended by two carbon atoms. The same transformation is also carried out using e.g. ethyl α-(phenylseleno)acetate as described in J. Am. Chem. Soc. 95, 6137 (1973). Similarly, the compounds of formula Ia wherein C represents halomethyl may first be converted to the corresponding carboxaldehydes with e.g. dimethylsulfoxide in the presence of triethylamine and silver tetrafluoroborate, or with chromium trioxide and pyridine in methylene chloride. Subsequent Wittig condensation e.g. with trimethylphosphonoacetate or ethyl (triphenylphosphorarylidene)acetate also yields the above-cited α,β-unsaturated esters.

Compounds of formula I wherein B is lower alkoxycarbonyl may be treated with ammonia, mono- or di-(lower) alkylamines e.g. methylamine, dimethylamine in an inert solvent, e.g. a lower alkanol, such as butanol, optionally at elevated temperatures to yield compounds of formula I wherein B represents unsubstituted, mono- or di(lower) alkylcarbamoyl.

Compounds of formula I wherein A contains straight chain or branched alkenylene with a terminal double bond, e.g. α, β-unsaturated esters, may also be prepared from the corresponding α, β-unsaturated compounds by treatment with e.g. phenylselenyl chloride in the presence of a strong base according to the procedure described in J. Am. Chem. Soc. 95, 6137 (1973).

Conversion of compounds of formula I wherein B is lower alkoxycarbonyl; cyano; unsubstituted, mono- or di-(loweralkyl) carbamoyl to compounds of formula I wherein B represents carboxy is advantageously carried out by hydrolysis with inorganic acids such as hydrohalic or sulfuric acid or with aqueous alkalies, preferably alkali metal hydroxides such as lithium or sodium hydroxide.

Compounds of formula I wherein B represents carboxy or lower alkoxycarbonyl may be reduced with simple or complex light metal hydrides such as lithium aluminum hydride, alane or diborane to compounds of formula I wherein B is hydroxymethyl. Said alcohols are also obtained by appropriate solvolysis of compounds of formula Ia wherein C is halomethyl by treatment with e.g. in alkali metal hydroxide such as lithium or sodium hydroxide.

Said alcohols may in turn be transformed to the compounds of formula I wherein B is carboxy with conventional oxidizing agents, advantageously with pyridinum dichromate in dimethylformamide at room temperature.

Free carboxylic acids may be esterified with lower alkanols such as ethanol in the presence of a strong acid, e.g. sulfuric acid, advantageously at elevated temperature or with diazo (lower) alkanes, e.g. diazomethane in a solvent such as ethyl ether, advantageously at room temperature, to give the corresponding esters, namely compounds of formula I wherein B is lower alkoxycarbonyl.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di-(lower) alkylamines, in an inert solvent such as methylene chloride, preferably in the presence of a basic catalyst such as pyridine, to compounds of formula I wherein B represents unsubstituted, mono or di-(lower)-alkylcarbamoyl.

Compounds of formula I wherein B represents mono(lower)-alkylcarbamoyl are converted to compounds of formula I wherein B is di-(lower)alkyl-carbamoyl by treatment of the former with a strong base e.g. sodium hydride followed by an alkylating agent, e.g. a lower alkyl halide in an inert solvent, e.g. dimethylformamide.

Furthermore compounds of formula I wherein A represents a straight chain or branched alkynylene or alkenylene may be converted by catalytic hydrogenation, advantageously under neutral conditions e.g. with palladium catalyst at atmospheric pressure in an inert solvent, e.g. ethanol, to compounds of formula I wherein A represents straight chain or branched alkylene.

The carboxaldehydes, the compounds of formula I wherein B represents formyl, may be prepared by oxidizing compounds of formula Ia wherein C represents respectively hydroxymethyl or halomethyl with e.g. dimethyl sulfoxide and a catalyst, such as a mixture of triethylamine and silver tetrafluoroborate, or with chromium trioxide and pyridine or other oxidizing agents known in the art. Said carboxaldehydes are converted to the corresponding acetals, the compounds of formula Ia wherein C represents di(lower)alkoxymethyl, or alkylenedioxymethyl e.g. a dimethylacetal, by acid-catalyzed condensation with an alcohol, e.g. methanol.

Compounds of formula I wherein B represents carboxy may be converted by the well-known Arndt-Eistert synthesis to compounds of formula I wherein B represents carboxy and the chain has been extended by 1 carbon atom. More particularly, a reactive functional derivative of the starting carboxylic acid, e.g. the acid chloride, is treated with diazomethane in e.g. diethyl ether to yield a compound of formula Ia wherein C represents diazoacetyl. Rearrangement with e.g. silver oxide yields said carboxylic acid of formula I wherein the chain has been extended by 1 carbon atom.

A specific embodiment of process (5) is for the preparation of compounds of formula I wherein B represents carboxy, and comprises converting, in a compound of the formula Ia in which C represents a functionally modified carboxyl group, the group C into carboxy, optionally by extending the chain A within its definition.

Groups convertible into a carboxy group are, for example, esterified carboxy groups, carboxy groups in form of their anhydrides, including corresponding groups of asymmetrical and inner anhydrides, amidated carboxy groups, cyano, amidino groups, including cyclic amidino group such as 5-tetrazolyl, iminoether groups, including cyclic iminoether groups, e.g., 2-oxazolinyl or dihydro-2-oxazolinyl groups substituted by lower alkyl, and also methyl, hydroxymethyl, etherified hydroxymethyl, lower alkanoyloxymethyl, trialkoxymethyl, acetyl, trihaloacetyl, halomethyl, carboxycarbonyl (COCOOH), formyl (CHO), di(lower)alkoxymethyl, alkylenedioxymethyl, vinyl, ethynyl or diazoacetyl.

Simultaneously with conversion of C into the carboxy group, the chain a can be extended within its definition.

Esterified carboxy groups are preferably carboxy groups in form of the lower alkyl esters, e.g. the methyl, ethyl, n- or i-(propyl or butyl) esters; substituted lower alkyl esters e.g. the ω-amino, ω-mono- or dimethylamino, α-carboxy or α-carbethoxy-(ethyl, propyl or butyl) esters; aryl(lower)alkyl esters, e.g. benzyl, (methyl-, methoxy-, chloro-)substituted benzyl, and pyridylmethyl esters; lower alkanoyloxy-(lower)alkyl esters, e.g. pivaloyloxymethyl esters; 3-phthalidyl and (methyl-, methoxy-, chloro-)substituted 3-phthalidyl esters, derived from the corresponding 3-hydroxyphthalides, (hydroxy-, lower alkanoyl-oxy-, lower alkoxy-) substituted lower alkoxymethyl esters e.g. β-(hydroxy-, acetyloxy-, methoxy-) ethoxymethyl esters; bicycloalkyloxy-carbonyl-(lower) alkyl esters, e.g. those derived from bicyclic monoterpenoid alcohols, such as unsubstituted or lower alkyl substituted bicyclo [2,2-]heptyloxycarbonyl-(lower)alkyl esters, advantageously bornyloxycarbonylmethyl esters; halo substituted lower alkyl esters, e.g. trichloroethyl or iodoethyl esters.

Amidated carboxy groups are preferably carboxy groups in form of their unsubstituted amides; N-mono or di-lower alkylamides, e.g. mono- or di-methylamides; tertiary amides derived from e.g. pyrrolidine, piperidine or morpholine; α-(lower) carboalkoxy- or carboxy-substituted lower alkylamides, e.g. mono N-(carboethoxymethyl)-amides, and mono N-(carboxy-methyl)amides; α-(lower) carboalkoxy or carboxy-substituted aryl-(lower) alkylamides, e.g. (carboethoxy or carboxy) substituted phenethylamides; amino(lower)-alkylamides, e.g. β-aminoethyl-amides and β-(carbobenzyloxy-amino)ethylamides.

The conversion into the carboxy group is accomplished by methods which are known per se, and as described herein and in the examples, e.g., solvolysis such as hydrolysis or acidolysis as previously described, or by reduction (esterified carboxy groups). For example, a trichloroethyl or 2-iodoethyl ester may be converted into the carboxylic acid by reduction, e.g. with zinc and a carboxylic acid in the presence of water. Benzyl esters or nitrobenzyl esters may be converted into the carboxy group by catalytic hydrogenation, the latter also with chemical reducing agents, e.g., sodium dithionite or with zinc and a carboxylic acid. In addition, tert-butyl esters may also be cleaved with trifluoroacetic acid. During the reduction of the group C, an alkenylene or alkynylene chain A may be converted into the corresponding alkylene chain.

Furthermore, compounds of formula Ia wherein C represents acetyl may be oxidatively cleaved to the corresponding compounds of formula I wherein B represents carboxy by conversion first to a compound of formula Ia wherein C represents trihaloacetyl, e.g. tribromo or triiodoacetyl, by treatment e.g. with sodium hypobromite followed by cleavage with e.g. an aqueous base, such as sodium hydroxide.

The starting materials of formula Ia wherein C represents acetyl are in turn prepared from compounds of formula Ia wherein C represents halomethyl by treatment with an alkyl ester of acetoacetic acid, e.g. ethyl acetoacetate, in the presence of a base, e.g. sodium hydride, followed by hydrolysis with a strong base, e.g., aqueous sodium hydroxide.

Said compounds are also prepared by condensing a compound of formula Ia wherein C is cyano with e.g. a Grignard or other organometallic reagent, e.g. methyl magnesium bromide under standard conditions.

Compounds of formula Ia wherein C represents carboxy-carbonyl (COCOOH) are converted thermally or by oxidation to compounds of formula I wherein B represents carboxy by heating at elevated temperature e.g., at about 200 degrees, in the presence of glass powder, or by treating e.g., with hydrogen peroxide in the presence of a basic agent, e.g. sodium hydroxide.

The starting materials of formula Ia wherein C represents COCOOH are prepared by e.g. condensation of a compound of formula Ia wherein C represents halomethyl with e.g. 2-ethoxycarbonyl-1,3-dithiane, and subsequent oxidative hydrolysis, e.g. with N-bromosuccinimide in aqueous acetone followed by treatment with dilute aqueous sodium hydroxide.

Compounds of formula Ia wherein C represents formyl, di(lower)alkoxymethyl or alkylenedioxymethyl (formyl protected in the form of an acetal), e.g. the dimethyl acetal, are oxidized with e.g. silver nitrate, pyridinium dichromate or ozone to the corresponding compound of formula I wherein B represents carboxy.

Compounds of formula Ia wherein C represents vinyl may be converted to compounds of formula I wherein B represents carboxy by first ozonolysis to compounds of formula I wherein B represents formyl, which are in turn oxidized to compounds of formula I wherein B represents carboxy.

Compounds of formula Ia wherein C represents vinyl may also be treated with nickel carbonyl and carbon monoxide under high pressure conditions to give compounds of formula I wherein B represents carboxy and the chain A contains a double bond adjacent to the carboxyl group.

Compounds of formula Ia wherein C represents ethynyl may be treated with a strong base, e.g. butyl lithium followed by condensation with carbon dioxide or condensation with a lower alkyl haloformate, e.g. ethyl chloroformate followed by hydrolysis to give compounds of formula I wherein B represents carboxy and the chain A contains a triple bond adjacent to the carboxyl group.

Compounds of formula Ia wherein C represents halomethyl may be converted to a corresponding organometallic intermediate, e.g. a cuprous or magnesium derivative, under conditions well known to the art.

Condensation of e.g. the resulting organomagnesium (Grignard) reagent, e.g. a compound of formula Ia wherein C is transformed to e.g. $CH_2MgCl$, with carbon dioxide yields a compound of formula I wherein B represents carboxy and the chain has been extended by 1 carbon atom.

Condensation of said Grignard reagent with e.g. a lower alkyl haloacetate or e.g. ethyl bromoacetate and subsequent hydrolysis yields a compound of formula I wherein B represents carboxy and wherein the chain has been extended by 2 carbon atoms.

Said Grignard reagent may be condensed in the presence of a cuprous halide, e.g. cuprous chloride, with an $\alpha,\beta$-unsaturated acid, e.g. propiolic or acrylic acid to yield a compound of formula I wherein B represents carboxy and wherein the chain has been extended by 3 carbon atoms.

Furthermore, compounds of formula Ia wherein C represents halomethyl may be condensed with e.g. the 3-lithio derivative of propiolic acid (prepared with e.g. lithium diisopropylamide) to yield a compound of formula I wherein A contains a terminal alkynylene, B represents carboxy and the chain length has been extended by 3 carbon atoms.

Compounds of formula I wherein A represents lower alkylene and B represents hydroxymethyl, as reactive functional derivatives thereof, may be condensed with a lower alkanol (or thiol), or a phenol (or thiophenol) appropriately substituted by B, preferably in the presence of a strong base, to give compounds of formula I wherein A represents lower alkylene-(thio or oxy)-phenylene, or lower alkylene-(thio or oxy)-lower alkylene.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel staring materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of optical isomers such as racemates, mixtures of diastereoisomers, mixtures of racemates or mixtures of geometrical isomers. The aforesaid possible isomers or mixtures thereof are within the purview of this invention; certain particular isomers may be preferred.

Any resulting mixtures of diastereoisomers, mixtures of racemates and geometric isomers can be separated on the basis of the physicochemical differences of the constituents, in known manner, into the pure isomers, diastereoisomers, racemates, or geometric isomers, for example by chromatography and/or fractional crystallisation.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification. The basic racemic products can likewise be resolved into the optical antipodes, e.g. by separation of the diastereoisomeric salts thereof, with an optically active acid, and liberating the optically active basic compound by treatment with a standard base. Racemic products of the invention can thus be resolved into their optical antipodes, e.g. by the fractional crystallization of d- or l-(tartrates, mandelates, camphorsulfonates), or of d- or l-(α-methylbenzylamine, cinchonidine, cinchonine, quinine, quinidine, ephedrine, dehydroabietylamine, brucine or strychnine) salts. Advantageously, the more active of the two antipodes is isolated.

Finally the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, and parenteral administration to mammals, including man, for the treatment of prevention of diseases responsive to inhibition of thromboxane synthetase, comprising an effective amount of a pharmacologically active compound of formula I, or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethylene-glycol; for tablets also (c) binders, e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

A mixture of 10.32 g of phenylhydrazine hydrochloride and 16.8 g of 7-nicotinoylheptanoic acid in 750 ml of ethanol is heated at refux temperature for 6 hours. After cooling with an ice-water bath, 250 ml of ca 2N ethanolic hydrogen chloride is added and the mixture heated at reflux for 16 hours. The mixture is filtered and the filtrate is concentrated under reduced pressure. The crude product is triturated with petroleum ether and recrystallized from ethanol-ether to yield 2-(3-pyridyl)-3-[5-(ethoxycarbonyl)-pentyl]-indole hydrochloride, m.p. 145°–150°.

The starting material is prepared as follows:

To a suspension of 16 g of 50% sodium hydride in 450 ml of ether is added dropwise 92.2 g of diethyl suberate and 27.3 ml (30.2 g) of ethyl nicotinate at room temperature, under nitrogen. The reaction mixture is heated at reflux temperature overnight, and, after cooling, 400 ml of ice water is added. The ether layer is separated (discarded) and the aqueous adjusted to pH 5 with 1N hydrochloric acid and extracted with ether (3×250 ml). The ether layer is dried and concentrated to give ethyl 7-ethoxycarbonyl-7-nicotinoylheptanoate as an oil. A solution of this ester in 300 ml of 1M sulfuric acid is heated for 12 hours at reflux temperature. The reaction solution is cooled by an ice bath and adjusted to pH=4.5–5.0 with saturated sodium bicarbonate solution. A white solid is collected and, after washing with water and air-drying, is recrystallized from ethanol to give 7-nicotinoylheptanoic acid, m.p. 113°–115°.

EXAMPLE 2

A solution of 7.46 g of 2-(3-pyridyl)-3-[5-(ethoxycarbonyl)-pentyl]-indole in 2N aqueous hydrochloric acid (275 ml) is heated at reflux for 20 hours. The hot reaction mixture is filtered, and the filtrate on cooling gives yellow crystals which are collected by filtration and dried to yield 2-(3-pyridyl)-3-(5-carboxypentyl)-indole hydrochloride, m.p. 220°–222°.

An aqueous solution of 10.5 g of 2-(3-pyridyl)-3-(5-carboxypentyl)-indole hydrochloride is neutralized to about pH 7 with saturated sodium bicarbonate solution and extracted with ether. The ether extract is dried and concentrated in vacuo to yield 2-(3-pyridyl)-3-(5-carboxypentyl)-indole.

EXAMPLE 3

To a suspension of 1.2 g of sodium hydride (60% in mineral oil) in 50 ml of DMF under nitrogen is added dropwise a solution of 8.8 g of 2-(3-pyridyl)-3-(5-carboxypentyl)-indole in 50 ml of dimethylformamide (DMF) at room temperature. After addition, the mixture is stirred for 0.5 hours, cooled to 0°–5°, and treated with 1.62 ml of methyl iodide. The mixture is stirred overnight, poured into ice water and acidified with 1N hydrochloric acid. After extraction with ether, the aqueous layer is adjusted to pH 9–10 with saturated sodium bicarbonate solution and extracted with 2×300 ml of ether. The ether layer is washed with brine, dried (MgSO$_4$) and concentrated to give an oil.

A solution of the residue in 300 ml of 2N hydrochloric acid is heated at reflux temperature for two hours. After concentration in vacuo sodium bicarbonate solution is added to adjust the pH to 5.5–6.5. The gummy solid which forms is extracted into methylene chloride. The organic layer is dried and evaporated and the residue is crystallized from acetonitrile to give 1-methyl-2-(3-pyridyl)-3-(5-carboxypentyl)-indole, m.p. 128°–130°.

EXAMPLE 4

(a) Analogous to the procedure of Example 1, condensation of p-methoxyphenylhydrazine with 7-nicotinoylheptanoic acid yields 2-(3-pyridyl)-3-[5-(ethoxycarbonyl)-pentyl]-5-methoxyindole hydrochloride, m.p. 152°–154°.

(b) Subsequent hydrolysis according to the procedure of Example 2 yields 2-(3-pyridyl)-3-(5-carboxypentyl)-5-methoxyindole, m.p. 185°–187°.

EXAMPLE 5

A solution of 1.5 g of 2-(3-pyridyl)-3-[5-(ethoxycarbonyl)-pentyl]-5-methoxyindole in 15 ml of 48% hydrobromic acid is treated at reflux temperature for 2.5 hours. The reaction solution is cooled and neutralized with sodium bicarbonate solution to pH 6–7, and then extracted with ethyl acetate. The organic extract is dried (MgSO$_4$), filtered, and concentrated to give a solid which is recrystallized from acetonitrile to give 5-hydroxy-2-(3-pyridyl)-3-(5-carboxypentyl)-indole, m.p. 185°–187°.

EXAMPLE 6

A mixture of 9.60 g of 7-nicotinoylheptanoic acid and 7.34 g of 4-chlorophenylhydrazine in 100 ml of ethanol is stirred and refluxed under nitrogen overnight. The reaction mixture is concentrated in vacuo to give a gum, which is suspended in 100 ml of ethanol, treated with 40 ml of 6N ethanolic hydrogen chloride, and refluxed under nitrogen for 22 hours. The suspension is cooled and an additional 50 ml of 6N ethanolic hydrogen chloride is added. Refluxing is resumed and continued for about 20 hours. The suspension is cooled in an ice-water bath and filtered. The filtrate is concentrated in vacuo to give a partially solid residue, which is triturated with ether-ethanol (10:1) and the yellow solid formed is collected to give 5-chloro-3-[5-(ethoxycarbonyl)pentyl]-2-(3-pyridyl)indole hydrochloride, m.p. 141°–145°.

Hydrolysis with 2N aqueous hydrochloric acid as described in Example 2 yields 5-chloro-3-(5-carboxypenthyl)-2-(3-pyridyl)-indole hydrochloride, m.p. 255°–257°.

EXAMPLE 7

To a suspension of sodium hydride in 10 ml of dry DMF while stirring under nitrogen at 0° is added dropwise a solution 2.12 g of 5-chloro-3-[5-(ethoxycarbonyl)-pentyl]-2-(3-pyridyl)-indole in DMF. Upon complete addition the orange suspension is stirred at 0° for 0.5 hours. To the suspension is added 0.42 ml. of iodomethane. The suspension is allowed to warm to room temperature. After stirring overnight at room temperature the reaction mixture is poured into water (80 ml) and extracted with ether (3×50 ml). The ether extract is washed with water and a saturated sodium chloride solution, dried (MgSO$_4$), filtered, and concentrated in vacuo to give 5-chloro-3-[5-(ethoxycarbonyl)-phenyl]-1-methyl-2-(3-pyridyl)indole.

EXAMPLE 8

A mixture of 1.0 g of 5-chloro-3-[5-(ethoxycarbonyl)-pentyl]-1-methyl-2-(3-pyridyl)indole in 20 ml of 2N aqueous hydrochloride acid is stirred and heated at reflux overnight. The mixture is cooled and the solid formed collected and dried in vacuo to give 5-chloro-3-(5-carboxypentyl)-1-methyl-2-(3-pyridyl)indole hydrochloride, m.p. 186°–189°.

EXAMPLE 9

(a) A solution of 3-(4-cyanobenzyl)-2-(3-pyridyl)indole (5.8 g) in 100 ml of a 1:1 mixture of 20% aqueous hydrochloric acid and glacial acetic acid is heated at reflux for 20 hours. After cooling, the solution is poured into ice water (100 ml) and the pH is adjusted to 4.5–5 with saturated sodium bicarbonate solution. The resulting precipitate is extracted with ethyl acetate, the ethyl acetate extract is washed with water and evaporated to dryness to give 3-(4-carboxybenzyl)-2-(3-pyridyl)indole.

The starting nitrile is prepared as follows:

To 30 ml of a 2M solution of ethylmagnesium bromide in tetrahydrofuran (THF) under nitrogen at 0°–5° is added dropwise over 20 minutes a solution of 10.0 g of 2-(3-pyridyl)indole in 60 ml of tetrahydrofuran. The reaction mixture is stirred for 0.5 hour at 0°–5° followed by dropwise addition of 9.8 g of p-cyanobenzyl bromide in 50 ml of tetrahydrofuran. After stirring at 0°–10° for 1 hour and at room temperature for 0.5 hour, the reaction mixture is poured into ice-water (600 ml). The resulting solid is collected, dried, washed with petroleum ether and redissolved in ether (500 ml). The ether solution is first washed with water, then with saturated sodium bicarbonate solution, dried over MgSO$_4$, treated with charcoal and filtered. Evaporation of the ether extract to dryness yields after purification 3-(4-cyanobenzyl)-2-(3-pyridyl)indole.

(b) Similarly prepared is 3-(4-carboxybenzyl)-5-chloro-2-(3-pyridyl)-indole.

EXAMPLE 10

(a) To a suspension of 0.49 g of lithium aluminum hydride in 50 ml of anhydrous tetrahydrofuran under nitrogen is added dropwise at room temperature a solution of 4.09 g of 3-(5-ethoxycarbonylpentyl)-5-chloro-1-methyl-2-(3-pyridyl)indole in 30 ml of anhydrous tetrahydrofuran. After addition is complete the suspension is stirred for 1 hour at room temperature, and 50 ml of a saturated ammonium chloride solution is added. The reaction mixture is allowed to stand at room temperature overnight and the organic layer is separated. The aqueous layer is filtered to remove salts and extracted with ethyl acetate (2×50 ml). The combined organic layers are washed with saturated brine, dried over magnesium sulfate and concentrated in vacuo. The crude product is purified by trituration with hexane/ether and dissolved in ethanol. Ethanolic hydrochloric acid is added to acidity and the solution diluted with anhydrous ether to crystallize the product. 3-(6-Hydroxyhexyl)-5-chloro-1-methyl-2-(3-pyridyl)indole hydrochloride is obtained.

(b) Similarly prepared is 3-(6-hydroxyhexyl)-1-methyl-2-(3-pyridyl)indole.

EXAMPLE 11

To a suspension of 1.52 g of 3-(5-carboxypentyl)-5-chloro-1-methyl-2-(3-pyridyl)indole in 50 ml of toluene under nitrogen is added dropwise at room temperature 0.31 ml of thionyl chloride. The resulting mixture is heated under reflux for 1 hour. An additional 0.10 ml portion of thionyl chloride is added and the solution is stirred at room temperature overnight. The resulting suspension is evaporated to dryness to give 3-(5-chlorocarbonylpentyl)-5-chloro-1-methyl-2-(3-pyridyl)indole. A suspension of the acid chloride in 20 ml of concentrated ammonium hydroxide is stirred at room temperature overnight. The resulting solid is filtered off to yield 3-(5-carbamoylpentyl)-5-chloro-1-methyl-2-(3-pyridyl)indole.

EXAMPLE 12

A solution of 4 g of 3-(5-ethoxycarbonylpentyl)-1-methyl-2-(3-pyridyl)indole in 40 ml of n-butanol is saturated with methylamine and heated on a steam bath in a pressure bottle for 3 days. The reaction mixture is evaporated to dryness and the product is crystallized from ethyl-ether to yield the 3-[5-(N-methylcarbamoyl)pentyl]-1-methyl-2-(3-pyridyl)indole.

EXAMPLE 13

A solution of 50 mg of 3-(5-carbamoylpentyl)-5-chloro-1-methyl-2-(3-pyridyl)indole in 1 ml of 6N HCl is heated at reflux temperature for 3 hours. On cooling the hydrochloride salt precipitates. The suspension is concentrated to dryness and the residue basified with saturated NaHCO$_3$ solution. This solution is washed with ether and neutralized to pH 6–7 with 2N HCl. Extraction with methylene chloride yields 3-(5-carboxypentyl)-5-chloro-1-methyl-2-(3-pyridyl)indole.

EXAMPLE 14

To 30 ml of a 2M solution of ethylmagnesium bromide in tetrahydrofuran under nitrogen at 0°–5° is added dropwise over 30 minutes a solution of 10.0 g of 2-(3-pyridyl)indole in 60 ml of tetrahydrofuran. The mixture is stirred for 0.5 hour at 0°–5° followed by the dropwise addition of 17.6 g of 1-tetrahydropyranyloxy-8-bromooctane in 50 ml of tetrahydrofuran. After stirring at 0°–10° for 1 hour and at room temperature for 0.5 hour, the reaction mixture is poured into ice-water and extracted with ether. The ether extract is washed with water, dried over MgSO$_4$ and evaporated to dryness. The residue is dissolved in 100 ml of 3N hydrochloric acid, the resulting mixture is kept at room temperature for 0.5 hour, washed with ether, basified with aqueous with 3N sodium hydroxide solution and extracted with methylene chloride. The methylene chloride solution is evaporated to dryness to give 3-(8-hydroxyoctyl)-2-(3-pyridyl)-indole.

EXAMPLE 15

To 12.0 ml of a 2M solution of ethylmagnesium bromide in tetrahydrofuran under nitrogen at 0°–5° is added dropwise over 20 minutes a solution of 4.0 g of 2-(3-pyridyl)indole in 20 ml of tetrahydrofuran. The mixture is stirred for 0.5 hours at 0°–5° and then is added a solution of 5.06 g of ethyl p-(2-bromoethoxy)benzoate [for preparation see U.S. Pat. No. 2,790,825 (1957)] in 30 ml of tetrahydrofuran. The suspension is stirred at 0°–10° for 1 hour and at room temperature for 0.5 hour, poured into ice-water and extracted with ether. The ether extract is separated, dried over MgSO$_4$, and concentrated to give 3-[2-(4-ethoxycarbonylphenoxy)ethyl]-2-(3-pyridyl)-indole.

EXAMPLE 16

A mixture of 4.5 g of 3-[2-(4-ethoxycarbonylphenoxy)ethyl]-2-(3-pyridyl)-indole in 220 ml of 2N hydrochloric acid is heated under reflux for 6 hours. After cooling the solution is made basic with 3N NaOH and extracted with ethyl acetate. The basic solution is filtered and acidifed to pH 6–7 with 3N NCl. The solid is collected and dried to give 3-[2-(4-carboxyphenoxy)ethyl]-2-(3-pyridyl)-indole.

EXAMPLE 17

A solution of 5.9 g of p-mercaptobenzoic acid ethyl ester (prepared according to the procedure found in J. Chem. Soc., 1963, 1947–1954) in 30 ml of dimethylformamide is added dropwise to a slurry of 1.55 g of 50% sodium hydride (dispersion in mineral oil) in 30 ml of dimethylformamide. This mixture is stirred at room temperature for 0.5 hour under nitrogen atmosphere, and added dropwise to a solution of 9.78 g of 3-(2-methylsulfonyloxyethyl)-2-(3-pyridyl)-indole in 60 ml of dimethylformamide at −10°. This mixture is stirred at room temperature overnight and poured into 1 liter of ice-water. This is extraced several times with ether. The ether extract is washed with water, dried over MgSO$_4$ and evaporated in vacuo to give 3-[2-(4-ethoxycarbonylphenylthio)-ethyl]-2-(3-pyridyl-indole.

The starting material can be prepared as follows:

To 10.0 g of 3-(2-ethoxycarbonylethyl)-2-(3-pyridyl)indole in 400 ml of dry tetrahydrofuran at 0° is added 60 ml of a 1M solution of lithium aluminum hydride in tetrahydrofuran. This is allowed to stir at room temperature for 1 hour, then cooled by an ice bath and quenched successively with 2.26 ml of water, 2.26 ml of a 15% sodium hydroxide solution, and 6.78 ml of water. The mixture is filtered, concentrated in vacuo, and the residue dissolved in ether, washed with a saturated NaHCO$_3$ solution, dried over MgSO$_4$ and concentrated in vacuo to give 3-(2-hydroxyethyl)-2-(3-pyridyl)-indole.

Methanesulfonyl chloride (2.50 ml) is added dropwise to a solution of 7.5 g 3-(2-hydroxyethyl)-2-(3-pyridyl)-indole and 10.0 ml of triethylamine in 150 ml of methylene chloride at −10°. This mixture is stirred at room temperature for 0.5 hour and poured into 600 ml of ice water. The resulting slurry is extracted with methylene chloride and the extract is washed with saturated sodium bicarbonate solution, dried over MgSO$_4$ and evaporated in vacuo to give 3-(2-methylsulfonyloxyethyl)-2-(3-pyridyl)-indole.

EXAMPLE 18

A mixture of 6.0 g of 1-[2-(4-ethoxycarbonylphenylthio)ethyl]-2-(3-pyridyl)-indole in 250 ml of 2N HCl is heated at reflux temperature for 6 hours. After cooling the pH is adjusted to 6–7 with saturated aqueous sodium bicarbonate (ca 500 ml). The resulting product is collected, first washed with water, then ether, and then dissolved in 100 ml hot absolute ethanol. The solution is filtered, and while still hot treated with 1.68 ml of 6.5N ethanolic HCl. The solution is cooled and diluted with ca 100 ml ether. The resulting 3-[2-(4-carboxyphenylthio)ethyl]-2-(3-pyridyl)-indole hydrochloride is collected.

EXAMPLE 19

A solution of lithium diisopropylamide (LDA) is prepared by adding n-butyl lithium (7.66 mmol, 1.6M in hexane) to a solution of diisopropylamine (7.6 mmol) in tetrahydrofuran (THF, 12 ml) at −20°. The LDA solution is cooled to −78° and 3-(5-ethoxycarbonylpentyl)-2-(3-pyridyl)-1-methylindole (2.48 g) in THF (24 ml) is added dropwise over 5 minutes. The mixture is stirred at −78° for 20 minutes, followed by addition of phenylselenyl chloride (1.5 g) in THF (12 ml). After 5 minutes the cooling bath is removed and the mixture allowed to warm to 0°. Saturated aqueous sodium bicarbonate (60 ml) is added, followed by ether extraction (3×50 ml). The combined organic phases are washed with saturated aqueous sodium bicarbonate, brine and then dried over anhydrous magnesium sulfate. Concentration in vacuo gives crude 3-(5-ethoxycarbonyl-5-phenylselenylpentyl)-2-(3-pyridyl)-1-methylindole. The crude selenide is dissolved in dichloromethane (40 ml) and 30% hydrogen peroxide (1.8 g, 16 mmol) in water (1.8 ml) is added dropwise. An exotherm begins after the addition of ca. 10% of the hydrogen peroxide. The temperature rise to 30° by completion of the addition. Stirring is continued for an additional 30 minutes, then 5% aqueous sodium carbonate (40 ml) is added. The dichloromethane layer is separated. The aqueous phase is extracted with dichloromethane (25 ml). The combined organic phases are washed with 5% aqueous sodium carbonate, water, brine, and dried over anhydrous magnesium sulfate. Concentration in vacuo yields 3-(5-ethoxycarbonylpent-4-enyl)-2-(3-pyridyl)-1-methylindole.

EXAMPLE 20

To a solution of the $\alpha,\beta$-unsaturated ester 3-(5-ethoxycarbonylpent-4-enyl)-2-(3-pyridyl)-1-methylindole (84 mg) in methanol (1 ml) is added 1N aqueous lithium hydroxide (1 ml). The mixture is stirred at room temperature overnight, then evaporated to dryness in vacuo. The residue is dissolved in water (2 ml) and washed with diethyl ether (5 ml). The aqueous phase is acidified to pH 6.6–7.0 and extracted with dichloromethane. The organic extract is washed with brine and dried over magnesium sulfate, then concentrated in vacuo to 3-(5-carboxypent-4-enyl)-2-(3-pyridyl)-1-methylindole.

EXAMPLE 21

To a solution of Collins Reagent prepared with chromium trioxide (5.6 g) and pyridine (8.86 g, 112 mmol) in dichloromethane (150 ml) at 0°–5° under a nitrogen atmosphere is added all at once 1.8 g of 3-(6-hydroxyhexyl)-1-methyl-2-(3-pyridyl)-indole in dichloromethane (15 ml). The mixture is stirred for an additional 30 minutes, the filtered through celite. The filtrate is then passed through a silica gel column. The product is eluted from the silica gel with a mixture of ethyl acetate:dichloromethane (500 ml). Concentration in vacuo yields 3-(5-formylpentyl)-2-(3-pyridyl)-1-methylindole.

EXAMPLE 22

Trimethyl phosphonoacetate (328 mg) is added dropwise to a solution of potassium tert-butoxide (220 mg) in THF (5 ml) of 0° under a nitrogen atmosphere. The solution is stirred at 0° for 20 minutes, then cooled to −78°. A solution of 3-(5-formylpentyl)-2-(3-pyridyl)-1-methylindole (450 mg) in THF (5 ml) is added dropwise over 15 minutes. The mixture is kept at −78° for 15 minutes, then the cooling bath is removed. The mixture is stirred overnight at room temperature, then diluted with water (25 ml) and extracted with diethyl ether (3×25 ml). The combined extracts are washed with saturated sodium bicarbonate, then brine, and dried over anhydrous magnesium sulfate. Concentration in vacuo yields the $\alpha,\beta$ unsaturated ester, 3-(7-methoxycarbonylhept-6-enyl)-2-(3-pyridyl)-1-methylindole.

EXAMPLE 23

Hydrolysis of 50 mg of 3-(7-methoxycarbonylhept-6-enyl)-2-(3-pyridyl)-1-methylindole with 1N aqueous lithium hydroxide yields 3-(7-carboxyhept-6-enyl)-2-(3-pyridyl)-1-methylindole.

EXAMPLE 24

3-(7-Carboxyhept-6-enyl)-2-(3-pyridyl)-1-methylindole (100 mg) is dissolved in 10 ml of absolute ethanol with a catalytic amount of 10% palladium of charcoal and hydrogenated at 1 atmosphere pressure. After 1 mole of hydrogen is consumed, the catalyst is removed by filtration and washed with a few milliliters of ethanol. The combined filtrates are concentrated in vacuo to yield 3-(7-carboxyheptyl)-1-methyl-2-(3-pyridyl)indole.

EXAMPLE 25

3-(4-Cyanobutyl)-2-(3-pyridyl)-indole (540 mg) is heated at 185° for 0.5 hour with 450 mg of powdered NaOH and 5 ml of ethylene glycol; the reaction solution is diluted with 50 ml water, washed with ether, and adjusted to pH 6 with 2N HCl, to give 3-(4-carboxybutyl)-2-(3-pyridyl)indole.

The starting material is prepared as follows:

To 6.0 ml of a 2M solution of ethylmagnesium bromide in tetrahydrofuran under nitrogen at 0° is added dropwise over 20 minutes a solution of 2-(3-pyridyl)indole (1.9 g) in 12 ml of tetrahydrofuran. The mixture is stirred at 0° for 0.5 hour and is then treated with a solution of 1.78 g of 5-bromovaleronitrile in 4 ml of tetrahydrofuran. This mixture is stirred at 0° for 1 hour, then at room temperature for 1 hour, and is then poured into 125 ml of ice-water. This is extracted with 2×50 ml of ether, the extract is washed with water, dried, evaporated to dryness and purified to give 3-(4-cyanobutyl)-2-(3-pyridyl)indole.

EXAMPLE 26

A mixture of 540 mg of 3-(4-cyanobutyl)-2-(3-pyridyl)indole, 173 mg of sodium azide, 142 mg of ammonium chloride and 5 mg of lithium chloride in 2 ml of DMF is heated at 120° overnight. After cooling the mixture is filtered and the filtrate diluted with ca. 25 ml of water. After the pH is adjusted to 10–11 with 3N NaOH, the solution is washed with ether to remove unreacted nitrile. The aqueous phase is adjusted to pH 5–6 with 2N HCl and extracted with ether. The ether extract is washed with water, dried over MgSO$_4$ and concentrated in vacuo. The residue is purified to give 3-[4-(5-tetrazolyl)-butyl]-2-(3-pyridyl)indole.

EXAMPLE 27

To 6.0 ml of a 2M solution of ethylmagnesium bromide in tetrahydrofuran under nitrogen at 0° is added dropwise over 20 minutes a solution of 2-(3-pyridyl)indole (1.9 g) in 12 ml of tetrahydrofuran. After complete addition the mixture is stirred at 0° for 0.5 hour and is then treated dropwise with a solution of 2.39 g of ethyl 3-(p-chloromethylphenyl)-2-methylacrylate in 5 ml of tetrahydrofuran. The resulting mixture is stirred at 0° for 1 hour, then at room temperature for 1 hour, and poured in 100 ml of ice-water. The resulting mixture is extracted with ether (2×50 ml) and the organic layer is washed with 100 ml of brine, dried over magnesium sulfate and evaporated to yield 3-[p-(2-ethoxycarbonyl-propen-1-yl)benzyl]-2-(3-pyridyl)indole.

(b) Hydrolysis with 2N aqueous hydrochloric acid yields 3-[p-(2-carboxy-propen-1-yl)benzyl]-2-(3-pyridyl)indole.

The starting material is prepared as follows:

To a suspension of 10.0 g of 50% sodium hydride (dispersion in mineral oil) in freshly distilled dimethyoxyethane (DME, 350 ml) stirred under nitrogen at 10° is added 53.6 ml of triethyl 2-phosphonopropionate in ca. 40 minutes. The mixture is stirred for 0.5 hour at 10° and for an additional 1.5 hours during which time the temperature is allowed to rise to room temperature. This solution is transferred under nitrogen by cannula to a 500 ml addition funnel and is added dropwise to a solution of terephthalaldehyde (33.53 g) in dry DME (475 ml) over a period of 1 hour at 22–341. After addition is complete the reaction mixture is stirred mechanically at room temperature for 2 hours, poured into 1L of water and extracted with 4×500 ml of ether. The ether extract is washed with a saturated sodium chloride solution (700 ml), dried over magnesium sulfate, filtered, and concentrated in vacuo to give a yellow oil which partially crystallizes on standing. This crude mixture is purified by suspending in petroleum ether and ethyl acetate (93:7). The filtrate, after removal of unreacted dialdehyde, is concentrated in vacuo to give a mixture which is further purified by high pressure liquid chromatography (using petroleum ether/ethyl acetate 93:7). There is obtained pure ethyl 4-formyl-α-methylcinnamate. A solution of the aldehyde (34.80 g) in 820 ml of absolute ethanol is treated with 12.11 g of granular sodium borohydride at room temperature under nitrogen. The resulting mixture is stirred at room temperature for 3 hours (or until all borohydride has dissolved) and then concentrated to ca. 200 ml volume, diluted with 400 ml of water, and extracted with 3×200 ml of ether. The ether extract is washed with 100 ml of water and brine (100 ml), is dried over magnesium sulfate, filtered, and the filtrate concentrated in vacuo to give ethyl 3-(p-hydroxymethylphenyl)-2-methylacrylate. To a solution of this product in 350 ml of methylene chloride is added at room temperature 11.53 ml of thionyl chloride dropwise over 25 minutes. The clear, colorless solution is stirred for 2 hours. The solution is washed with 100 ml of water, 200 ml of saturated sodium bicarbonate, 100 ml of water, and 100 ml of brine. The organic layer after drying and removal of solvent yields ethyl 3-(p-chloromethylphenyl)-2-methylacrylate which can be used without further purification.

EXAMPLE 28

3-(5-Formylpentyl)-1-methyl-2-(3-pyridyl)indole (127 mg) is dissolved in DMF (0.66 ml) and pyridinium dichromate (298 mg) added all at once. The mixture is stirred overnight at room temperature, then diluted with ether and filtered. The solid is washed with methylene chloride and the combined filtrates concentrated in vacuo to yield a product which is extracted into 0.1 N aqueous sodium hydroxide (2 ml). The aqueous extract is acidified to pH 5.5–6.0 and extracted with chloroform. The chloroform extract is dried and concentrated with vacuo yielding after purification by chromatography 3-(5-carboxypentyl)-2-(3-pyridyl)-1-methylindole of Example 3.

EXAMPLE 29

A solution of 3-(5-carboxypentyl)-5-chloro-1-methyl-2-(3-pyridyl)indole hydrochloride (400 mg) in 7 ml of tetrahydrofuran is warmed and treated with 200 mg (0.27 ml) of triethylamine. This solution is added dropwise to a solution of 108 mg (0.096 ml) of ethyl chloroformate in 1 ml of tetrahydrofuran which is cooled to 0°–5°. The reaction mixture is stirred 1 hour at this temperature and filtered to remove triethylamine hydrochloride. The filtrate is treated with a solution of hydroxylamine hydrochloride (69 mg) and sodium hydroxide (40 mg) in 10 ml of methanol. This mixture is stirred 0.5 hr and concentrated in vacuo. The residue is treated with 25 ml of ether-methanol (10:1) and filtered. The filtrate is evaporated in vacuo, the residue is dissolved in acetone and treated with 6.5N ethanolic HCl to give 3-(5-hydroxycarbamoylpentyl)-5-chloro-1-methyl-2-(3-pyridyl)-indole hydrochloride.

EXAMPLE 30

3-[7,7-(bis-methoxycarbonyl)heptyl]-1-methyl-2-(3-pyridyl)indole (273 mg) is dissolved in methanol (0.5 ml) and 1 N aqueous lithium hydroxide (1.95 ml) added. The mixture is stirred at room temperature for 1 hour, then refluxed for 2.5 hours. The solution is concentrated to dryness, and the residue dissolved in water and the pH adjusted to 6–6.2. The mixture is extracted into methylene chloride. Concentration of the extract, after drying over anhydrous magnesium sulfate, yields crude 3-[7,7-(bis-carboxy)-heptyl]-1-methyl-2-(3-pyridyl) indole.

A sample of the crude dicarboxylic acid (30 mg) is heated with p-xylene (3 ml) containing 0.1 N HCl (0.1 ml) for 0.5 hour. The reaction mixture is allowed to cool to room temperature and is extracted into aqueous sodium hydroxide. The aqueous phase is separated, and after adjustment of the pH to 6–6.2, extracted with ethyl acetate. The organic phase is dried over anhydrous magnesium sulfate and concentrated to give 3-(7-carboxyheptyl)-1-methyl-2-(3-pyridyl)-indole.

The starting material is prepared as follows:

Thionyl chloride (0.36 ml) is combined with 3-(6-hydroxyhexyl)-1methyl-2-(3-pyridyl)indole (1.37 g) at 0°. The mixture is then stirred at room temperature for 1 hour. Saturated aqueous sodium bicarbonate is added and the mixture is extracted with dichloromethane. The extract is washed with brine, dried over anhydrous magnesium sulfate and concentrated in vacuo to yield the crude chloride, 3-(6-chlorohexyl)-1-methyl-2-(3-pyridyl)indole. 3-(6-Chlorohexyl)-1-methyl-2-(3-pyridyl)indole (0.5 g) is combined with dimethyl malonate (792 mg), potassium carbonate (790 mg) and dimethylformamide (11.6 ml) and the mixture is heated at 80°–90° for 18 hours under nitrogen. The mixture is poured into ice water (80 ml), and acidified with 1N NCl and washed with ether. The aqueous layer is adjusted to pH 6 and extracted with ether which is then dried over anhydrous magnesium sulfate and concentrated to yield 3-[7,7-(bis-methoxycarbonyl)heptyl]-1-methyl-2-(3-pyridyl)indole.

EXAMPLE 31

3-(6-Chlorohexyl)-1-methyl-2-(3-pyridyl)indole (165 mg) in dry THF (2 ml) is added dropwise to magnesium turnings (12 mg) in dry THF (2 ml) under a nitrogen atmosphere. A crystal of iodine is added during the addition to initiate the reaction. The mixture is refluxed for 4 hours after the addition is completed, then cooled to 0°, and dry carbon dioxide gas bubbled into the flask with stirring for 15 minutes. The mixture is poured into 5 ml of 1 N NaOH and extracted with ether. The aqueous phase is adjusted to pH 6–6.2and extracted with ethyl acetate. The organic phase is dried over anhydrous magnesium sulfate and concentrated in vacuo yielding 3-(6-carboxyhexyl)-1-methyl-2-(3-pyridyl)indole.

EXAMPLE 32

To 30 ml of 2M solution of ethylmagnesium bromide in tetrahydrofuran under nitrogen at 0°–5° is added dropwise over 30 minutes a solution of 10.0 g of 2-(3-pyridyl)indole in 60 ml of tetrahydrofuran. The mixture is stirred fo 0.5 hour at 0°–5° followed by the dropwise addition of 10.6 g of methyl bromotetrolate (J. Chem. Soc. 1950, 3646) in50 ml of tetrahydrofuran. The mixture is stirred for an additional 2 hours, at 0° poured into ice water, and extracted with ether. The aqueous phase is extracted with ether. The ether extract is washed with water, brine, and dried over anhydrous magnesium sulfate. Concentration in vacuo yields 3-(3-methoxycarbonyl-prop-2-ynyl)-2-(3-pyridyl)indole.

EXAMPLE 33

Treatment of 330 mg of 3-(3-methoxycarbonylprop-2-ynyl)-2-(3-pyridyl)indole in 10 ml of methanol with 3.0 ml of aqueous 1N lithium hydroxide at room temperature yields 3-(3-carboxyprop-2-ynyl)-2-(3-pyridyl)indole.

EXAMPLE 34

(a) To a solution of ethyl-4-(3-indolyl)butyrate (3.00 g) and imidazole (4.43 g) in dioxane (75 ml) stirring at 10° is added dropwise while stirring a solution of bromine (0.65 ml) in dioxane (25 ml) over a period of 2.5 hours. Immediately upon the addition of bromine the reaction mixture becomes a thick suspension. Additional dioxane (30 ml) is added to keep the reacton mixture more mobile. Upon complete addition to cooling bath is removed and the reaction mixture allowed to stir at room temperature overnight. The suspended solid is removed by vacuum filtration and the filtrate concentrated in vacuo to give an orange oil. This oil is suspended in either (100 ml) and extracted with 1N hydrochloric acid (1×50 ml). The aqueous layer is washed with ether (1×100 ml), made basic with 3 N sodium hydroxide (12 ml), and extracted with ether (2×100 ml). This ether extract is washed with brine, dried (MgSO4), filtered, and concentrated in vacuo to give an orange oil which becomes partially crystalline.

This material (1.38 g) is dissolved in 20 ml ether and to the solution is added 0.65 ml of 7.1M ethanolic hydrogen chloride. The salt separates as an oil which crystallizes on addition of a few milliliters of ethanol to yield 2-(1-imidazolyl)-3-(-3-ethoxycarbonylpropyl)indole hydrochloride, m.p. 152°–155°.

(b) Similarly prepared is 2-(1-imidazolyl)-3-(5-ethoxycarbonylpentyl)indole; NMR (CDCl$_3$): 4.07 (q, 2H), 1.23 (t, 3H), 7.0–7.8 (m, 7H).

EXAMPLE 35

(a) A suspension of 0.20 g of 2-(1-imidazolyl-3-(3-ethoxycarbonylpropyl)indole hydrochloride in 5 ml of 3N NaOH is stirred at room temperature for 2 hours. Absolute ethanol (5 ml) is then added and the resulting solution is stirred an additional 2.5 hours at room temperature. The solution is concentrated in vacuo in order to remove ethanol. The resulting solution is acidified to pH 3.5 with 1N HCl. The precipitate is collected and dried (50°/25 mm Hg) to give 2-(1-imidazolyl)-3-(3-caboxypropyl)indole, m.p. 205°–207°.

(b) Similarly prepared is 2-(1-imidazolyl)-3-(5carboxypentyl)indole, m.p. 146°–148°.

EXAMPLE 36

To a suspenion of (4carboxybutyl)triphenylphosphonium bromide (4.17 g) in toluene (50 ml) while stirring under nitrogen at room temperature is added potassium t-butoxide (2.11 g). The suspension is heated to and maintained at 90° for 40 minutes. The resulting suspension is cooled to room temperature, and a solution of 1-methyl-2-(3-pyridyl)indole-3-carboxaldehyde (2.00 g) in a mixture of toluene (20 ml) and dimethylsulfoxide (4 ml) is added dropwise. After complete addition the suspension is stirred overnight at room temperature.

The reaction mixture is heated at 60° for 3 hours, cooled to room temperature and diluted with water (100 ml). The organic layer is separated and removed. The aqueous layer is first extracted with toluene (1×100 ml) and ether (1×100 ml), acidified to pH 1 with 1 N HCl and then extracted with ether (2×100 ml). The ether extract is dried (MgSO4), filtered, and concentrated in vacuo to give an oil. Purification by flash chromatography over silica gel with methylene chloride/MeOH (97:3) yields essentially pure 3-(5-carboxypent-1-enyl)-1-methyl-2-(3-pyridyl)indole which is converted to the hydrochloride salt. This is recrystallized from methanol/ether to give 3-(5-carboxypent-1-enyl)-1-methyl-2-(3-pyridyl)indole hydrochloride, m.p. 163°–165°.

The starting material is prepared as follows:

A solution of 19.7 of phenylhydrazine (21.63 g) and 22 ml of 3-acetylpyridine (24.23 g) in glacial acetic acid (100 ml) is stirred and refluxed for 4.5 hours. The solution is cooled in an ice-water bath and neutralized with a saturated sodium bicarbonate solution (180 ml). The precipitate is collected, washed and dried to give 3-acetylpyridine phenylhydrazone.

A mixture of the hydrazone (8.0 g) and polyphosphoric acid (74.0 g) is stirred and heated on a steam bath for 1 hour. The mixture is then heated at 135°–140° for 10 minutes. The reaction mixture is poured into 840 ml of water and the precipitate is collected and washed with water. The product is again suspended in 100 ml of ice water and the pH adjusted to 8 with 50% aqueous sodium hydroxide. The precipitate is collected, washed with cold water, and dried to give 2-(3-pyridyl)indole, m.p. 176°–177°. [Ref. Bull Soc. Chim. France, 1969, 4154].

Phosphorus oxychloride (3.36 ml) is added dropwise over a period of 20 minutes to dimethylformamide (10.6 g) maintained at 0°–3°. After complete addition a solution of 2-(3-pyridyl)indole (6.50 g) in dimethylformamide (20 ml) is added dropwise over a period of 30 minutes at such a rate so that the reaction temperature does not exceed 10°. The cooling bath is then removed and the viscous solution heated to and maintained at 35°–40° for 1 hour. The reaction mixture is treated with crushed ice (50 g). A solution of sodium hydroxide (24.4 g) in 65 ml of water is added slowly. After the addition the resulting red-orange solution is heated rapidly to reflux and maintained at reflux for about 2 minutes. The solution is allowed to cool to room temperature, then placed in a freezer for 2 days. The resulting precipitate is collected and washed well with water to give an orange solid which is recrystallized from methanol (240 ml) to give 2-(3pyridyl)-indole-3-carboxaldehyde, m.p. 236°–238°.

To a solution of 2-(3pyridyl) indole-3-carboxaldehyde (2.22 g) in dimethylformamide (20 ml) under nitrogen at room temperature is added potassium carbonate (3.97 g). The suspension is stirred at room temperature for 5 minutes. Iodomethane (1.56 g) is added in one portion and the resulting suspension is stirred at room temperature overnight. The suspension is then diluted with water (100 ml); and solid is collected, washed with water and dried to give 1-methyl-2-(3-pyridyl)indole-3-carboxyaldehyde, m.p. 148°–150°.

EXAMPLE 37

A solution of 3-(5-carboxypent-1-enyl)-1-methyl-2-(3-pyridyl)indole (0.51 g) in absolute ethanol (20 ml), to which is added 10% Pd/C (0.05 g), is hydrogenated at 3 atmospheres pressure for 2 hours. The catalyst is removed by filtration and the filtrate concentrated to dryness. Trituration of the residue with absolute ethanol gives a while solid, m.p. 117°–120°. Recrystallization from acetonitrile yields 1-methyl-2-(3-pyridyl)-3-(5-carboxypentyl)indole (the compound of Example 3), m.p. 128°–130°.

EXAMPLE 38

Preparation by methods analogous to those described in the previous examples of additional compounds of formula II and formula III wherein $R_1'=CH_3$ and $R_4=OH$.

| Compound | $R_2'$ | $R_3'$ | $(CH_2)_m$ |
|---|---|---|---|
| 1 | 5-Cl | H | $(CH_2)_7$ |
| 2 | H | H | $(CH_2)_4$ |
| 3 | 5-Cl | 6-Cl | $(CH_2)_5$ |
| 4 | 5-F | H | $(CH_2)_5$ |
| 5 | 5-CH$_3$ | H | $(CH_2)_5$ |
| 6 | 5-CH$_3$ | H | $(CH_2)_7$ |
| 7 | H | H | $(CH_2)_{10}$ |
| 8 | 5-O—CH$_2$—O—6 | | $(CH_2)_5$ |
| 9 | 5-OH | H | $(CH_2)_5$ |
| 10 | 5-SCH$_3$ | H | $(CH_2)_5$ |
| 11 | H | H | $(CH_2)_{11}$ |
| 12 | H | H | $(CH_2)_9$ |

EXAMPLE 39

Preparation by methods analogous to those described in the previous examples of additional compounds of formula I wherein $R_1=CH_3$, Ar=3-pyridyl or 1-imidazolyl, and B=COOH

| Example | $R_2$ | $R_3$ | A |
|---|---|---|---|
| 1 | H | H | $CH_2—C\equiv C—(CH_2)_2$ |
| 2 | H | H | $CH_2—S—(CH_2)_2$ |
| 3 | H | H | $(CH_2)_2—O—(CH_2)_2$ |
| 4 | H | H | $CH_2—O—(CH_2)_3$ |

EXAMPLE 40

Preparation of 10,000 tablets each containing 10 mg of the active ingredient:
Formula:
3-(5-carboxypentyl)-1-methyl-2-(3-pyridyl)indole: 100.00 g
Lactose: 1,157.00 g
Corn starch: 75.00 g
Polyethylene glycol 6,000: 75.00 g
Talcum powder: 75.00 g
Magnesium stearate: 18.00 g
Purified water: q.s.
Procedure:

All of the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave with 6.4 mm diameter, uppers bisected.

EXAMPLE 41

Preparation of 10,000 capsules each containing 25 mg of the active ingredient:
Formula:
3-(5-carboxypentyl)-1-methyl-2-(3-pyridyl)indole: 250.0 g
Lactose: 1,650 g
Talcum powder: 100.0 g
Procedure:

All the powders are passed through a screen with openings of 0.6 mm. Then the drug substance is placed in a suitable mixer and mixed first with the talcum, then with the lactose until homogeneous. No. 3 capsules are filled with 200 mg, using a capsule filling machine.

Similarly prepared are tablets and capsules comprising about 10-100 mg of other compounds of the invention, e.g. any other compound given in the examples herein.

What is claimed is:

1. A compound of the formula

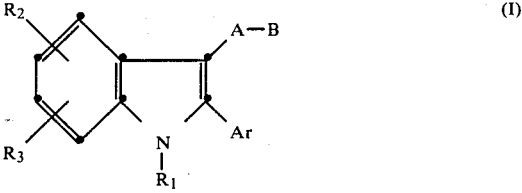

wherein $R_1$ represents hydrogen or lower alkyl;

Ar represents 3-pyridyl or 1-imidazolyl, each unsubstituted or substituted by lower alkyl, carboxy, lower alkoxycarbonyl or carbamoyl;

$R_2$ and $R_3$ independently represent hydrogen, lower alkyl, halogen, trifluoromethyl, hydroxy, lower alkoxyl, carboxy-lower alkyl, lower alkoxycarbonyl-lower alkyl, carboxy, lower alkoxycarbonyl, or lower alkyl-(thio, sulfinyl or sulfonyl), or $R_2$ and $R_3$ together on adjacent carbon atoms represent lower alkylenedioxy;

A represents straight chain or branched alkylene of 3 to 12 carbon atoms in which the number of the carbon atoms separating the indole nucleus from group B is 3 to 12, straight chain or branched alkenylene of 2 to 12 carbon atoms, straight chain or branched alkynylene of 2 to 12 carbon atoms, lower alkylenephenyl-lower (alkylene or alkenylene,) lower alkylene-phenylene, lower alkylene-(thio or oxy)-lower alkylene, lower alkylene-(thio or oxy)-phenylene, or lower alkylene-phenylene(thio or oxy)-lower alkylene;

B represents carboxy, carboxy esterified in form of a pharmaceutically acceptable ester, carbamoyl, mono- or di-lower alkylcarbamoyl, hydroxymethyl, cyano, hydroxycarbamoyl, 5-tetrazolyl or formyl; the imidazolyl and pyridyl N-oxide thereof, or a pharmaceutically acceptable salt thereof.

2. A compound according to claim 1 wherein
$R_1$ represents hydrogen or lower alkyl;

Ar represents 3-pyridyl, 1-imidazolyl, 3-pyridyl substituted by lower alkyl, or 1-imidazolyl substituted by lower alkyl;

$R_2$ and $R_3$ independently represent hydrogen, lower alkyl, halogen, trifluoromethyl, hydroxy, lower alkoxy or lower alkylthio; or $R_2$ and $R_3$ together on adjacent carbon atoms represent lower alkylenedioxy;

A represents straight chain alkylene of 4 to 12 carbon atoms, lower(alkylenephenylene, alkylene-thio-phenylene or alkylene-oxy-phenylene) of 7 to 10 carbon atoms each;

B represents carboxy, lower alkoxycarbonyl, carbamoyl, cyano, hydroxycarbamoly, 5-tetrazolyl, or hydroxymethyl; or a pharmaceutically acceptable salt thereof.

3. A compound according to claim 1 wherein A represents straight chain alkylene of 4 to 10 carbon atoms, lower alkylenephenylene of 7 to 10 to carbon atoms, lower alkylene-thio-phenylene of 7 to 10 carbon atoms or lower alkylene-oxy-phenylene of 7 to 10 carbon atoms; B represents carboxy or lower alkoxycarbonyl; Ar represents 3-pyridyl or 1-imidazolyl; $R_2$ and $R_3$ independently represent hydrogen, lower alkyl, halogen, trifluoromethyl, hydroxy, lower alkylthio or lower alkoxy; pharmaceutically acceptable salt thereof.

4. A compound according to claim 3 wherein A represents straight chain alkylene of 4 to 8 carbon atoms.

5. A compound according to claim 1 of the formula

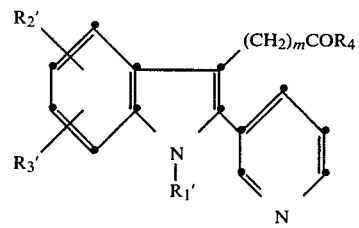

wherein
$R_1'$ represents hydrogen or lower alkyl;
$R_2'$ and $R_3'$ represent independently hydrogen, lower alkyl, halogen, trifluoromethyl, hydroxy, lower alkylthio or lower alkoxy; or $R_2'$ and $R_3'$ together on adjacent carbon atoms represent methylenedioxy;
m represents an integer from 4 to 12;
$R_4$ represent hydroxy, lower alkoxy or amino; or a pharmaceutically acceptable salt thereof.

6. A compound according to claim 5 wherein $R_1'$ represents hydrogen or lower alkyl; $R_2'$ represents hydrogen or halogen; $R_3'$ represents hydrogen; m is 4 to 8; $R_4$ represents hydroxy, lower alkoxy or amino; pharmaceutically acceptable salt thereof.

7. A compound according to claim 5 wherein $R_1$ represents hydrogen of methyl; $R_2'$ represents hydrogen or chloro; $R_3'$ represents hydrogen; m is 5; $R_4$ represents hydroxy; or a pharmaceutically acceptable salt thereof.

8. A compound according to claim 1 of the formula

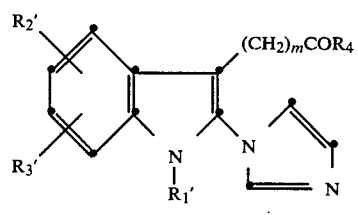

wherein
$R_1'$ represents hydrogen or lower alkyl;
$R_2'$ and $R_3'$ represent independently hydrogen, lower alkyl, halogen, trifluoromethyl, hydroxy, lower alkylthio or lower alkoxy; or $R_2'$ and $R_3'$ together on adjacent carbon atoms represent methylenedioxy;
m represents an integer from 3 to 12;
$R_4$ represents hydroxy, lower alkoxy or amino; or a pharmaceutically acceptable salt thereof.

9. A compound according to claim 8 wherein $R_1'$ represents hydrogen or lower alkyl; $R_2'$ represents a hydrogen or halogen; $R_3'$ represents hydrogen; m is 4 to 8; $R_4$ represents hydroxy, lower alkoxy or amino; or a pharmaceutically acceptable salt thereof.

10. A compound according to claim 8 wherein $R_1$ represents hydrogen or methyl; $R_2'$ represents hydrogen or chloro; $R_3'$ represents hydrogen; m is 5; $R_4$ represents hydroxy; or a pharmaceutically acceptable salts thereof.

11. A compound according to claim 5 being 2-(3-pyridyl)-3-(5-carboxypentyl)-indole or a pharmaceutically acceptable salt thereof.

12. A compound according to claim 5 being 1-methyl-2-(3-pyridyl)-3-(5-carboxypentyl)-indole or a pharmaceutically acceptable salt thereof.

13. A compound according to claim 5 being 5-chloro-1-methyl-2-(3-pyridyl)-3-(5-carboxypentyl)-indole or a pharmaceutically acceptable salt thereof.

14. A compound according to claim 8 being 2-(1-imidazolyl)-3-(3-carboxypropyl)-indole or a pharmaceutically acceptable salt thereof.

15. A compound according to claim 8 being 2-(1-imidazolyl)-3-(5-carboxypentyl)-indole or a pharmaceutically acceptable salt thereof.

16. A compound according to claim 8 being 2-(1-imidazolyl)-3-(3-ethoxycarbonylpropyl)-indole or a pharmaceutically acceptable salt thereof.

17. A pharmaceutical composition suitable for administration to mammals for the treatment of diseases responsive to inhibition of thromboxane synthetase comprising an effective amount of a compound of claim 1 in combination with one or more pharmaceutically acceptable carriers.

18. A method of selectively inhibiting the synthesis of thromboxane in a mammal comprising the administration to a mammal in need thereof of an effective amount of a compound of claim 1 in combination with one or more pharmaceutically acceptable carriers.

19. A method of treating diseases responsive to thromboxane synthetase inhibition in mammals comprising the administration to a mammal in need thereof of a therapeutically effective thromboxane synthetase inhibiting amount of a compound of claim 1 in combination with one or more pharmaceutically acceptable carriers.

20. A method of treating cardiovascular diseases in mammals comprising the administration to a mammal in need thereof of an effective thromboxane synthetase inhibiting amount of a compound of claim 1 in combination with one or more pharmaceutically acceptable carriers.

* * * * *